US012583869B2

(12) United States Patent
Chen et al.

(10) Patent No.: US 12,583,869 B2
(45) Date of Patent: Mar. 24, 2026

(54) SALT FORM AND CRYSTAL FORM OF A2A RECEPTOR ANTAGONIST AND PREPARATION METHOD THEREFOR

(71) Applicants: CSTONE PHARMACEUTICAL (SUZHOU) CO., LTD., Suzhou (CN); CSTONE PHARMACEUTICALS (SHANGHAI) CO., LTD., Shanghai (CN); CSTONE PHARMACEUTICALS, Grand Cayman (KY)

(72) Inventors: Kevin X Chen, Shanghai (CN); Kai Zhou, Shanghai (CN); Yanxin Yu, Shanghai (CN); Boyu Hu, Shanghai (CN); Li Zhang, Shanghai (CN); Zhaoguo Chen, Shanghai (CN)

(73) Assignees: CSTONE PHARMACEUTICAL (SUZHOU) CO., LTD., Suzhou (CN); CSTONE PHARMACEUTICALS (SHANGHAI) CO., LTD., Shanghai (CN); CSTONE PHARMACEUTICALS, Grand Cayman (KY)

( * ) Notice: Subject to any disclaimer, the term of this patent is extended or adjusted under 35 U.S.C. 154(b) by 1190 days.

(21) Appl. No.: 17/442,688

(22) PCT Filed: Mar. 27, 2020

(86) PCT No.: PCT/CN2020/081704

§ 371 (c)(1),
(2) Date: Sep. 24, 2021

(87) PCT Pub. No.: WO2020/192762

PCT Pub. Date: Oct. 1, 2020

(65) Prior Publication Data

US 2022/0185825 A1 Jun. 16, 2022

(30) Foreign Application Priority Data

Mar. 28, 2019 (CN) ......................... 201910244468.8

(51) Int. Cl.
*C07D 519/00* (2006.01)
*C07C 57/145* (2006.01)

(52) U.S. Cl.
CPC .......... *C07D 519/00* (2013.01); *C07C 57/145* (2013.01); *C07B 2200/13* (2013.01)

(58) Field of Classification Search
CPC ... C07D 519/00; C07B 2200/13; Y02A 50/30; A61P 35/00; C07C 57/145; C07C 309/04; C07C 309/30
See application file for complete search history.

(56) References Cited

U.S. PATENT DOCUMENTS

| | | | | |
|---|---|---|---|---|
| 6,514,989 B1 | 2/2003 | Nettekoven et al. | | |
| 11,312,715 B2 * | 4/2022 | Chen | .................... | C07D 471/04 |
| 2020/0239465 A1 | 7/2020 | Chen et al. | | |

FOREIGN PATENT DOCUMENTS

| | | | | |
|---|---|---|---|---|
| CN | 1541216 A | 10/2004 | | |
| CN | 105025899 A | 11/2015 | | |
| WO | WO-2015020565 A1 | 2/2015 | | |
| WO | WO-2019002606 A1 | 1/2019 | | |
| WO | WO-2019038214 A1 | 2/2019 | | |
| WO | WO-2019062803 A * | 4/2019 | ............ | A61K 31/00 |
| WO | WO-2019062803 A1 | 4/2019 | | |

OTHER PUBLICATIONS

Guerrero, Current Medicinal Chemistry, vol. 25, No. 30, 2018 (Year: 2018).*
Allard, Immunology and Cell Biology, vol. 95, Iss. 4, 2017 (Year: 2017).*
Jun. 24, 2020 International Search Report issued in International Patent Application No. PCT/CN2020/081704.
Jun. 24, 2020 Written Opinion of the International Searching Authority issued in International Patent Application No. PCT/CN2020/081704.
Extended European Search Report issued in European Patent Application No. 20778350 dated Nov. 4, 2022.
Serajuddin, Abu T M. "Salt formation to improve drug solubility." Advanced drug delivery reviews vol. 59,7 (2007): 603-16. doi:10.1016/j.addr.2007.05.010.
Byrn, S et al. "Pharmaceutical solids: a strategic approach to regulatory considerations." Pharmaceutical research vol. 12,7 (1995): 945-54. doi: 10.1023/a:1016241927429.
Stahl PH (2003) Preparation of water-soluble compounds through salt formation, in The Practice of Medicinal Chemistry, 2nd Edition (Wermuth CG ed) pp. 601-615, London, Elsevier.
Caira, M.R. (1998). Crystalline Polymorphism of Organic Compounds. Topics in Current Chemistry, 198, 163-208.

* cited by examiner

*Primary Examiner* — Susanna Moore
*Assistant Examiner* — Luisalberto Gonzalez

(57) ABSTRACT

Provided are a salt form and a crystal form of adenosine $A_{2A}$ receptor antagonist, and preparation method therefor. Also provided is an application of the salt form or crystal form in the preparation of a medicine for $A_{2A}$ receptor-related diseases, the maleate salt in the salt form has a structure of formula (I).

(I)

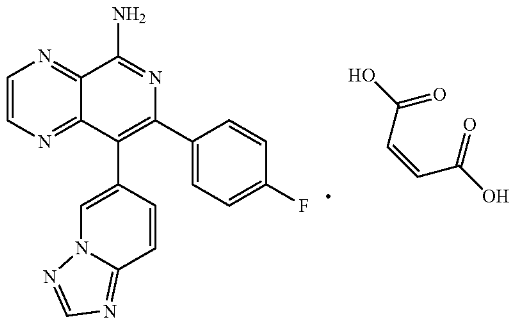

4 Claims, 8 Drawing Sheets

SALT FORM AND CRYSTAL FORM OF A2A RECEPTOR ANTAGONIST AND PREPARATION METHOD THEREFOR

CROSS-REFERENCE TO RELATED APPLICATIONS

This application is a U.S. National Phase Application under 35 U.S.C. 371 of International Application No. PCT/CN2020/081704, filed on Mar. 27, 2020, which claims the benefit of Chinese Patent Application No. 201910244468.8, filed on Mar. 28, 2019. The entire disclosures of the above applications are incorporated herein by reference.

TECHNICAL FIELD

The present disclosure relates to salt forms and crystal forms of adenosine $A_{2A}$ receptor antagonist and a preparation method thereof, and also includes the application of the salt forms and crystal forms in the preparation of medicaments for $A_{2A}$ receptor-related diseases.

BACKGROUND

Adenosine $A_{2A}$ receptors are widely distributed in human tissues. This receptor is highly expressed in tissues and organs such as spleen, thymus, white blood cells, platelets, GABA neurons and olfactory bulbs, etc. It is also expressed in other parts of the heart, lungs, blood vessels, and brain, etc. Adenosine $A_{2A}$ receptors generally coexist with other GPCR and combine to form heterodimers. For example, $A_{2A}$ receptors can form heterodimers with dopamine $D_2$, cannabinoid $CB_1$, glutamic acid mGluR5, etc. Adenosine $A_{2A}$ receptors play an important role in regulating vasodilation, supporting the formation of new blood vessels, and protecting body tissues from damage caused by inflammation; adenosine $A_{2A}$ receptors also affect the activity of indirect pathways in the basal ganglia.

In solid tumors, the decomposition of cell tissue and the hypoxic environment cause a large amount of ATP to decompose, which leads to the enrichment of extracellular adenosine, the concentration is abnormally high, which is 10-100 times of the normal value. The binding of high concentrations of adenosine and $A_{2A}$ receptor activates the adenosine signaling pathway. This signaling pathway is a mechanism that protects the body tissues through immunosuppression when the body tissues are damaged. The activation of the adenosine signaling pathway leads to a long-term suppression of the innate immune response. This long-term suppression can produce immune tolerance, the combination of adenosine and $A_{2A}$ receptors in white blood cells (e.g., lymphocytes, T-lymphocytes, natural killer cells, dendritic cells, etc.) inhibits the proper effector function of these white blood cells in the immune system, leading to uncontrolled growth of malignant tumors. The binding of adenosine to the $A_{2A}$ receptor increases the expression of CD39, CD73 and CTLA4 (T cell checkpoint), thereby generating more $T_{reg}$ cells with stronger immunosuppressive properties. Blocking the adenosine signaling pathway of the $A_{2A}$ receptor can reduce the inhibitory effect on the immune system and enhance the immune function of T cells, so it is considered to be a promising negative feedback mechanism that can inhibit tumor growth.

The monoclonal antibody CS1003 is a full-length, fully humanized immunoglobulin G4 (IgG4) monoclonal antibody against PD-1.

Content of the Present Invention

The present disclosure provides a compound of formula (I).

(I)

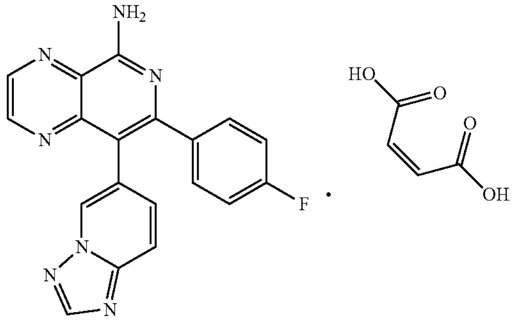

The present disclosure also provides a crystal form A of the compound of formula (I), wherein the X-ray powder diffraction pattern thereof has characteristic diffraction peaks at the following 2θ angles: 7.16±0.2°, 9.66±0.2°, 19.66±0.2°.

In some embodiments of the present disclosure, the X-ray powder diffraction pattern of the crystal form A has characteristic diffraction peaks at the following 2θ angles: 7.16±0.2°, 9.66±0.2°, 13.59±0.2°, 14.30±0.2°, 15.87±0.2°, 17.73±0.2°, 19.66±0.2°, 20.88±0.2°.

In some embodiments of the present disclosure, the X-ray powder diffraction pattern of the crystal form A has characteristic diffraction peaks at the following 2θ angles: 7.16±0.2°, 9.66±0.2°, 13.59±0.2°, 14.30±0.2°, 15.87±0.2°, 17.73±0.2°, 19.66±0.2°, 20.88±0.2°, 26.01±0.2°, 26.76±0.2°, 27.21±0.2°.

In some embodiments of the present disclosure, the XRPD pattern of the crystal form A is shown in FIG. 1.

In some embodiments of the present disclosure, the analysis data of the XRPD pattern of the crystal form A is shown in Table 1.

TABLE 1

Analysis data of the XRPD pattern of the crystal form A

| No. | 2θ angle (°) | d-spacing (Å) | Relative intensity (%) |
|---|---|---|---|
| 1 | 7.155 | 12.3452 | 79.4 |
| 2 | 7.624 | 11.5857 | 24.8 |
| 3 | 9.660 | 9.1484 | 92.7 |
| 4 | 11.160 | 7.9216 | 12.2 |
| 5 | 13.585 | 6.5125 | 44.7 |
| 6 | 14.298 | 6.1896 | 77.2 |
| 7 | 15.871 | 5.5794 | 45.7 |
| 8 | 16.501 | 5.3677 | 21.8 |
| 9 | 16.697 | 5.3051 | 14.2 |
| 10 | 17.154 | 5.1649 | 23.9 |
| 11 | 17.729 | 4.9988 | 66.3 |
| 12 | 18.966 | 4.6753 | 30.5 |
| 13 | 19.348 | 4.5838 | 41.4 |
| 14 | 19.660 | 4.5119 | 100.0 |
| 15 | 20.882 | 4.2505 | 58.6 |
| 16 | 21.728 | 4.0869 | 20.3 |
| 17 | 22.603 | 3.9305 | 20.1 |
| 18 | 23.050 | 3.8553 | 16.8 |
| 19 | 23.469 | 3.7875 | 24.2 |
| 20 | 25.501 | 3.4901 | 15.6 |
| 21 | 26.012 | 3.4227 | 58.4 |

TABLE 1-continued

| Analysis data of the XRPD pattern of the crystal form A | | | |
|---|---|---|---|
| No. | 2θ angle (°) | d-spacing (Å) | Relative intensity (%) |
| 22 | 26.759 | 3.3288 | 41.3 |
| 23 | 27.214 | 3.2741 | 60.1 |
| 24 | 27.951 | 3.1895 | 6.2 |
| 25 | 28.198 | 3.1621 | 5.5 |
| 26 | 28.849 | 3.0922 | 12.9 |
| 27 | 29.290 | 3.0466 | 13.4 |
| 28 | 29.624 | 3.0131 | 6.6 |
| 29 | 30.154 | 2.9612 | 5.5 |
| 30 | 30.689 | 2.9109 | 20.4 |
| 31 | 31.437 | 2.8433 | 5.2 |
| 32 | 31.772 | 2.8141 | 8.0 |
| 33 | 31.986 | 2.7957 | 5.5 |
| 34 | 33.233 | 2.6936 | 6.3 |
| 35 | 33.804 | 2.6494 | 6.6 |
| 36 | 34.374 | 2.6068 | 4.2 |
| 37 | 35.220 | 2.5461 | 3.1 |
| 38 | 35.560 | 2.5225 | 2.9 |
| 39 | 36.192 | 2.4799 | 3.5 |
| 40 | 36.563 | 2.4556 | 3.5 |
| 41 | 36.978 | 2.4290 | 4.8 |
| 42 | 38.181 | 2.3551 | 5.6 |
| 43 | 38.654 | 2.3274 | 3.0 |

In some embodiments of the present disclosure, the differential scanning calorimetry curve of the crystal form A has an endothermic peak at 205.67±3° C.

In some embodiments of the present disclosure, the DSC pattern of the crystal form A is shown in FIG. 2. In some embodiments of the present disclosure, the thermogravimetric analysis curve of the crystal form A has a weight loss of 0.1846% at 120.00° C.±3° C.

In some embodiments of the present disclosure, the thermogravimetric analysis curve of the crystal form A has a weight loss of 0.1846%±0.2% at 120.00° C.±3° C.

In some embodiments of the present disclosure, the TGA pattern of the crystal form A is shown in FIG. 3.

The present disclosure also provides a method for preparing the crystal form A of the compound of formula (I), comprising:

(a) adding the compound of formula (I) to a solvent;

(b) stirring at 30-50° C. for 40-55 hours;

(c) a solid separated by centrifugation is the crystal form A of the compound of formula (I);

wherein, the solvent is alcohol, acetonitrile, acetone, ethyl acetate, tert-butyl methyl ether, water, tetrahydrofuran, a mixed solvent of alcohol and water, and a mixed solvent of acetonitrile and water.

In some embodiments of the present disclosure, the alcohol is selected from methanol, ethanol, isopropanol and n-propanol, and other variables are as defined in the present disclosure.

In some embodiments of the present disclosure, in the mixed solvent of alcohol and water, the volume ratio of alcohol to water is 1:1, and other variables are as defined in the present disclosure.

In some embodiments of the present disclosure, in the mixed solvent of acetonitrile and water, the volume ratio of acetonitrile to water is 1:1, and other variables are as defined in the present disclosure.

The present disclosure also provides a use of the compound or the crystal form A or the crystal form A prepared according to the above method in manufacturing a medicament for the treatment of diseases related to $A_{2A}$ receptors.

The present disclosure also provides a crystal form B of a compound of formula (II), wherein the X-ray powder diffraction pattern thereof has characteristic diffraction peaks at the following 2θ angles: 12.84±0.2°, 15.84±0.2°, 23.55±0.2°.

(II)

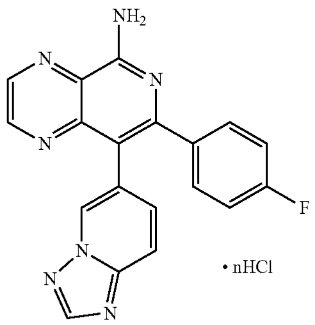

• nHCl n is selected from 0.5, 0.6, 0.7, 0.8, 0.9, 1.0, 1.1, 1.2, 1.3, 1.4, 1.5, 1.6, 1.7, 1.8, 1.9 and 2.0. In some embodiments of the present disclosure, the n is selected from 0.7 and 1, preferably 1.

In some embodiments of the present disclosure, the X-ray powder diffraction pattern of the crystal form B has characteristic diffraction peaks at the following 2θ angles: 6.43±0.2°, 11.22±0.2°, 12.84±0.2°, 15.84±0.2°, 19.78±0.2°, 21.61±0.2°, 23.55±0.2°, 27.02±0.2°.

In some embodiments of the present disclosure, the X-ray powder diffraction pattern of the crystal form B has characteristic diffraction peaks at the following 2θ angles: 6.43±0.2°, 11.22±0.2°, 12.41±0.2°, 12.84±0.2°, 15.84±0.2°, 16.36±0.2°, 19.27±0.2°, 19.78±0.2°, 21.61±0.2°, 23.55±0.2°, 27.02±0.2°, 28.62±0.2°.

In some embodiments of the present disclosure, the XRPD pattern of the crystal form B is shown in FIG. 4.

In some embodiments of the present disclosure, the analysis data the XRPD pattern of the crystal form B is shown in Table 2.

TABLE 2

| Analysis data of the XRPD pattern of the crystal form B | | | |
|---|---|---|---|
| No. | 2θ angle (°) | d-spacing (Å) | Relative intensity (%) |
| 1 | 6.425 | 13.7446 | 77.2 |
| 2 | 11.218 | 7.8807 | 55.7 |
| 3 | 12.405 | 7.1294 | 26.5 |
| 4 | 12.838 | 6.8901 | 100.0 |
| 5 | 15.836 | 5.5918 | 83.8 |
| 6 | 16.361 | 5.4134 | 10.1 |
| 7 | 17.931 | 4.9427 | 7.4 |
| 8 | 19.265 | 4.6033 | 18.6 |
| 9 | 19.779 | 4.4849 | 55.9 |
| 10 | 21.613 | 4.1083 | 82.0 |
| 11 | 23.545 | 3.7753 | 95.9 |
| 12 | 27.017 | 3.2976 | 66.2 |
| 13 | 28.616 | 3.1168 | 28.2 |
| 14 | 31.323 | 2.8534 | 8.9 |

In some embodiments of the present disclosure, the differential scanning calorimetry curve of the crystal form B has an onset of an endothermic peak at 256.37±3° C.

In some embodiments of the present disclosure, the DSC pattern of the crystal form B is shown in FIG. 5.

In some embodiments of the present disclosure, the thermogravimetric analysis curve of the crystal form B has a weight loss of 0.8860% at 159.53° C.±3° C.

In some embodiments of the present disclosure, the TGA pattern of the crystal form B is shown in FIG. 6.

The present disclosure also provides a crystal form C of a compound of formula (III), wherein the X-ray powder diffraction pattern thereof has characteristic diffraction peaks at the following 2θ angles: 15.56±0.2°, 20.23±0.2°, 24.51±0.2°.

(III)

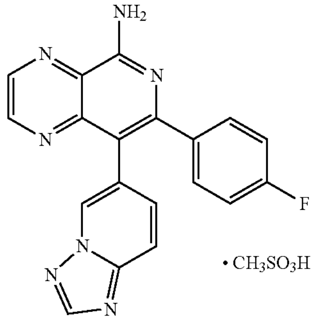

In some embodiments of the present disclosure, the X-ray powder diffraction pattern of the crystal form C has characteristic diffraction peaks at the following 2θ angles: 8.89±0.2°, 15.56±0.2°, 15.99±0.2°, 20.23±0.2°, 21.63±0.2°, 23.47±0.2°, 24.51±0.2°, 28.18±0.2°.

In some embodiments of the present disclosure, the X-ray powder diffraction pattern of the crystal form C has characteristic diffraction peaks at the following 2θ angles: 8.89±0.2°, 14.10±0.2°, 15.56±0.2°, 15.99±0.2°, 16.48±0.2°, 17.49±0.2°, 20.23±0.2°, 21.63±0.2°, 23.47±0.2°, 24.51±0.2°, 26.33±0.2°, 28.18±0.2°.

In some embodiments of the present disclosure, the XRPD pattern of the crystal form C is shown in FIG. 7.

In some embodiments of the present disclosure, the analysis data of the XRPD pattern of the crystal form C is shown in Table 3.

TABLE 3

Analysis data of the XRPD pattern of the crystal fonn C

| No. | 2θ angle (°) | d-spacing (Å) | Relative intensity (%) |
|---|---|---|---|
| 1 | 8.894 | 9.9347 | 24.8 |
| 2 | 14.10 | 6.2750 | 13.2 |
| 3 | 15.56 | 5.6901 | 66.7 |
| 4 | 15.99 | 5.5376 | 23.6 |
| 5 | 16.48 | 5.3736 | 15.3 |
| 6 | 17.49 | 5.0654 | 18.0 |
| 7 | 17.68 | 5.0116 | 11.7 |
| 8 | 18.57 | 4.7720 | 11.1 |
| 9 | 20.23 | 4.3853 | 75.5 |
| 10 | 21.63 | 4.1046 | 36.8 |
| 11 | 23.23 | 3.8257 | 7.1 |
| 12 | 23.46 | 3.7878 | 18.9 |
| 13 | 24.510 | 3.6288 | 100.0 |
| 14 | 25.243 | 3.5252 | 9.9 |
| 15 | 26.330 | 3.3821 | 15.3 |
| 16 | 26.801 | 3.3236 | 11.0 |
| 17 | 28.183 | 3.1637 | 21.9 |
| 18 | 29.801 | 2.9956 | 8.6 |
| 19 | 31.376 | 2.8486 | 12.0 |
| 20 | 33.339 | 2.6853 | 4.0 |
| 21 | 34.436 | 2.6022 | 4.8 |
| 22 | 34.698 | 2.5832 | 3.6 |
| 23 | 39.006 | 2.3072 | 3.7 |

In some embodiments of the present disclosure, the differential scanning calorimetry curve of the crystal form C has an onset of an endothermic peak at 269.72±3° C.

In some embodiments of the present disclosure, the DSC pattern of the crystal form C is shown in FIG. 8.

In some embodiments of the present disclosure, the thermogravimetric analysis curve of the crystal form C has a weight loss of 0.3017% at 144.33° C.±3° C. and a weight loss of 0.6266% at 200.08° C.±3° C.

In some embodiments of the present disclosure, the TGA pattern of the crystal form C is shown in FIG. 9.

The present disclosure also provides a crystal form D of a compound of formula (IV), wherein the X-ray powder diffraction pattern thereof has characteristic diffraction peaks at the following 2θ angles: 17.08±0.2°, 17.75±0.2°, 26.80±0.2°.

(IV)

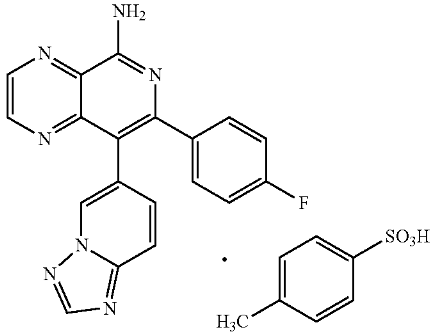

In some embodiments of the disclosure, the X-ray powder diffraction pattern of the crystal form D has characteristic diffraction peaks at the following 2θ angles: 13.31±0.2°, 16.66±0.2°, 17.08±0.2°, 17.75±0.2°, 22.58±0.2°, 23.63±0.2°, 24.95±0.2°, 26.80±0.2°.

In some embodiments of the present disclosure, the X-ray powder diffraction pattern of the crystal form D has characteristic diffraction peaks at the following 2θ angles: 12.38±0.2°, 13.31±0.2°, 16.66±0.2°, 17.08±0.2°, 17.75±0.2°, 18.65±0.2°, 22.58±0.2°, 23.63±0.2°, 24.95±0.2°, 25.40±0.2°, 26.80±0.2°, 27.65±0.2°.

In some embodiments of the present disclosure, the X-ray powder diffraction pattern of the crystal form D has characteristic diffraction peaks at the following 2θ angles: 4.433±0.2°, 12.38±0.2°, 13.31±0.2°, 16.66±0.2°, 17.08±0.2°, 17.75±0.2°, 18.65±0.2°, 22.58±0.2°, 23.63±0.2°, 24.95±0.2°, 25.40±0.2°, 26.80±0.2°, 27.65±0.2°.

In some embodiments of the present disclosure, the XRPD pattern of the crystal form D is shown in FIG. 10.

In some embodiments of the present disclosure, the analysis data of the XRPD pattern of the crystal form D is shown in Table 4.

TABLE 4

Analysis data of the XRPD pattern of the crystal fonn D

| No. | 2θ angle (°) | d-spacing (Å) | Relative intensity (%) |
|---|---|---|---|
| 1 | 4.433 | 19.9173 | 100.0 |
| 2 | 12.378 | 7.1447 | 16.9 |
| 3 | 12.681 | 6.9748 | 7.1 |
| 4 | 13.054 | 6.7763 | 19.5 |

TABLE 4-continued

Analysis data of the XRPD pattern of the crystal fonn D

| No. | 2θ angle (°) | d-spacing (Å) | Relative intensity (%) |
|---|---|---|---|
| 5 | 13.310 | 6.6465 | 28.5 |
| 6 | 13.766 | 6.4275 | 6.5 |
| 7 | 14.731 | 6.0084 | 8.9 |
| 8 | 16.663 | 5.3158 | 34.0 |
| 9 | 17.078 | 5.1877 | 83.8 |
| 10 | 17.748 | 4.9933 | 71.7 |
| 11 | 18.654 | 4.7529 | 27.1 |
| 12 | 20.996 | 4.2277 | 7.0 |
| 13 | 22.580 | 3.9346 | 39.3 |
| 14 | 23.627 | 3.7626 | 38.2 |
| 15 | 24.393 | 3.6460 | 12.3 |
| 16 | 24.947 | 3.5663 | 33.7 |
| 17 | 25.404 | 3.5031 | 23.6 |
| 18 | 26.388 | 3.3747 | 12.9 |
| 19 | 26.800 | 3.3238 | 46.7 |
| 20 | 27.651 | 3.2234 | 24.4 |
| 21 | 28.479 | 3.1316 | 6.2 |
| 22 | 28.732 | 3.1045 | 7.0 |
| 23 | 29.404 | 3.0351 | 7.5 |
| 24 | 31.394 | 2.8471 | 6.8 |
| 25 | 37.618 | 2.3891 | 4.5 |

In some embodiments of the present disclosure, the differential scanning calorimetry curve of the crystal form D has an onset of an endothermic peak at 238.96±3° C.

In some embodiments of the present disclosure, the DSC pattern of the crystal form D is shown in FIG. 11.

In some embodiments of the present disclosure, the thermogravimetric analysis curve of the crystal form D has a weight loss of 0.07607% at 109.87° C.±3° C. and a weight loss of 0.59157% at 223.14° C.±3° C.

In some embodiments of the present disclosure, the TGA pattern of the crystal form D is shown in FIG. 12.

The present disclosure also provides a use of the crystal form B of the compound of formula (II), the crystal form C of the compound of formula (III) and the crystal form D of the compound of formula (IV) in manufacturing a medicament for the treatment of $A_{2A}$ receptor-related diseases.

The present disclosure also provides a crystal form E of a compound of formula (V), wherein the X-ray powder diffraction pattern thereof has characteristic diffraction peaks at the following 2θ angles: 15.74±0.2°, 16.82±0.2°, 24.67±0.2°.

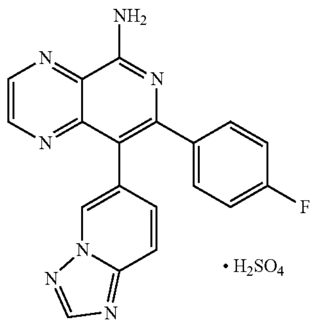

(V)

In some embodiments of the present disclosure, the X-ray powder diffraction pattern of the crystal form E has characteristic diffraction peaks at the following 2θ angles: 12.25±0.2°, 13.76±0.2°, 15.74±0.2°, 16.82±0.2°, 20.15±0.2°, 22.03±0.2°, 24.67±0.2°, 25.52±0.2°.

In some embodiments of the present disclosure, the X-ray powder diffraction pattern of the crystal form E has characteristic diffraction peaks at the following 2θ angles: 12.25±0.2°, 13.76±0.2°, 15.74±0.2°, 16.25±0.2°, 16.82±0.2°, 18.28±0.2°, 20.15±0.2°, 22.03±0.2°, 24.67±0.2°, 25.52±0.2°, 26.19±0.2°, 29.94±0.2°.

In some embodiments of the present disclosure, the XRPD pattern of the crystal form E is shown in FIG. 13.

In some embodiments of the present disclosure, the analysis data of the XRPD pattern of the crystal form E is shown in Table 5.

TABLE 5

Analysis data of the XRPD pattern of the crystal form E

| No. | 2θ angle (°) | d-spacing (Å) | Relative intensity (%) |
|---|---|---|---|
| 1 | 8.437 | 10.4709 | 13.0 |
| 2 | 12.246 | 7.2217 | 32.5 |
| 3 | 13.763 | 6.4291 | 39.4 |
| 4 | 14.784 | 5.9870 | 16.1 |
| 5 | 15.737 | 5.6267 | 51.1 |
| 6 | 16.247 | 5.4513 | 24.8 |
| 7 | 16.821 | 5.2663 | 93.3 |
| 8 | 18.281 | 4.8490 | 24.1 |
| 9 | 19.049 | 4.6550 | 21.7 |
| 10 | 20.153 | 4.4026 | 29.4 |
| 11 | 20.770 | 4.2732 | 7.7 |
| 12 | 22.028 | 4.0318 | 35.2 |
| 13 | 23.982 | 3.7076 | 13.0 |
| 14 | 24.671 | 3.6056 | 100.0 |
| 15 | 25.519 | 3.4877 | 26.9 |
| 16 | 26.189 | 3.3999 | 23.7 |
| 17 | 28.061 | 3.1772 | 19.2 |
| 18 | 29.442 | 3.0313 | 8.1 |
| 19 | 29.936 | 2.9824 | 26.8 |
| 20 | 31.141 | 2.8696 | 7.7 |
| 21 | 32.212 | 2.7766 | 5.1 |
| 22 | 32.527 | 2.7505 | 4.9 |
| 23 | 33.410 | 2.6798 | 12.3 |
| 24 | 33.760 | 2.6528 | 10.6 |
| 25 | 37.018 | 2.4264 | 5.1 |

In some embodiments of the present disclosure, the differential scanning calorimetry curve of the crystal form E has an endothermic peak at 257.96±3° C.

In some embodiments of the present disclosure, the DSC pattern of the crystal form E is shown in FIG. 14.

In some embodiments of the present disclosure, the thermogravimetric analysis curve of the crystal form E has a weight loss of 0.7061% at 63.75° C.±3° C. and a weight loss of 1.2632% at 155.23° C.±3° C.

In some embodiments of the present disclosure, the TGA pattern of the crystal form E is shown in FIG. 15.

The present disclosure also provides a use of the crystal form E of the compound of formula (V) in manufacturing a medicament for the treatment of diseases related to $A_{2A}$ receptors.

Technical Effect

The present disclosure synthesizes the compound of formula (I) to obtain a new class of adenosine $A_{2A}$ antagonist, which is used as a single agent or combined with an antibody for tumor immunotherapy. The compound of the present disclosure exhibits better solubility, along with significantly improves the pharmacokinetic properties.

The combination of the compound of the present disclosure and CS1003 achieves a good anti-tumor effect, and the combination of the compound of the present disclosure and CS1003 has a synergistic effect.

The compound of the present disclosure has sufficient exposure in plasma and tumor tissues.

The crystal forms of the compounds of the present disclosure have good stability under high temperature and high humidity conditions.

Definitions and Explanations

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions in the embodiments of the present disclosure are carried out in a suitable solvent, and the solvent should be suitable for the chemical change together with the reagents and materials required in the present disclosure. In order to obtain the compounds of the present disclosure, it is sometimes necessary for those skilled in the art to modify or select the synthetic steps or reaction schemes based on the existing embodiments.

The compounds of the present disclosure can be prepared by a variety of synthetic methods well known to those skilled in the art, including the specific embodiments listed below, the embodiments formed by their combination with other chemical synthesis methods, and equivalent alternatives well known to those skilled in the art, preferred embodiments include but are not limited to the embodiments of the present disclosure. The structure of the compound of the present disclosure can be confirmed by conventional methods well known to those skilled in the art. If the present disclosure relates to the absolute configuration of the compound, the absolute configuration can be confirmed by conventional technical means in the art. For example, the single crystal X-ray diffraction method (SXRD) uses the Bruker D8 venture diffractometer to collect the diffraction intensity data of the cultivated single crystal, the light source is CuKα radiation and the scanning mode is φ/ω scanning After collecting relevant data, the crystal structure is further analyzed by direct method (Shelxs97), and the absolute configuration can be confirmed.

All solvents used in the present disclosure are commercially available and can be used without further purification.

The present disclosure uses the following abbreviations: rt stands for room temperature; THF stands for tetrahydrofuran; NMP stands for N-methylpyrrolidone; $MeSO_3H$ stands for methanesulfonic acid; DME stands for ethylene glycol dimethyl ether; DCM stands for dichloromethane; Xphos stands for 2-Bicyclohexylphosphine-2'4'6'-triisopropylbiphenyl; EtOAc stands for ethyl acetate; MeOH stands for methanol; 2-Me-THF stands for 2-methyltetrahydrofuran; IPA stands for isopropanol; $Pd(dppf)_2Cl_2$ stands for [1,1'-bis(diphenylphosphino)ferrocene] palladium dichloride dichloromethane complex; RH stands for humidity; BID stands for twice a day.

The compounds are named according to the conventional naming principles in the art or using ChemDraw® software, and the commercially available compounds use the supplier catalog name.

X-Ray Powder Diffraction Analysis (X-Ray Powder Diffractometer, XRPD) of the Present Disclosure Instrument model: Bruker D8 advanced X-ray diffractometer Detection method: Approximately 10-20 mg of the sample was used for XRPD detection.

The detailed XRPD parameters are as follows:

Light pipe: Cu, kα, (λ=1.54056 Å).

Light tube voltage: 40 kV, light tube current: 40 mA

Divergence slit: 0.60 mm

Detector slit: 10.50 mm

Anti-scatter slit: 7.10 mm

Scanning range: 4-40 deg

Step diameter: 0.02 deg

Step time: 0.12 seconds

Rotation speed of sample tray: 15 rpm

Differential Scanning Calorimetry Analysis (Differential Scanning Calorimeter, DSC) of the Present Disclosure Instrument model: TA Q2000 Differential Scanning Calorimeter Detection method: A sample (about 1 mg) was placed in a DSC aluminum crucible for detection. Under the condition of 50 mL/min and $N_2$, at a heating rate of 10° C./min, the sample was heating from 30° C. (room temperature) to 300° C. (or 350° C.).

Thermogravimetric Analysis (Thermal Gravimetric Analyzer, TGA) of the Present Disclosure Instrument model: TA Q5000IR thermogravimetric analyzer Detection method: A sample (2-5 mg) was placed in a TGA platinum crucible for detection. Under the condition of 25 mL/min and $N_2$, at a heating rate of 10° C./min, the sample was heated from room temperature to 350° C. or had a weight loss of 20%.

High-Performance Liquid Chromatography Analysis Method (HPLC) of the Present Disclosure is Shown in Table 6

TABLE 6

Content detection of the compound of formula (I) and liquid chromatographic conditions for the analysis of related substances

| | | | |
|---|---|---|---|
| Equipment | High-performance liquid chromatography Shimadzu LC-20ADXR PDS-PF-HPLC-15 | | |
| chromatography column | Agilent Eclipse Plus C18 4.6 × 150 mm, 3.5 μm PDS-HPLC-150 | | |
| Mobile phase | A: 0.04% TFA in Water B: ACN | | |
| | Time (mm) | A | B |
| Gradient elution procedure | 0.01 | 90 | 10 |
| | 20.00 | 70 | 30 |
| | 30.00 | 10 | 90 |
| | 35.00 | 10 | 90 |
| | 35.01 | 90 | 10 |

TABLE 6-continued

| Content detection of the compound of formula (I) and liquid chromatographic conditions for the analysis of related substances | | | |
|---|---|---|---|
| | 40.01 | 90 | 10 |
| | 40.01 | STOP | |
| Running time | 40.01 min | | |
| Column temperature | 35° C. | | |
| Current Speed | 1 mL/min | | |
| Injection volume | 10 | | |
| Detection | PDA 190-400 nm; (250 nm for calculation) | | |
| Diluent | Acetonitrile: Pure water = 1:1 (v/v) | | |

DETAILED DESCRIPTION OF THE PREFERRED EMBODIMENT

Figure 1:
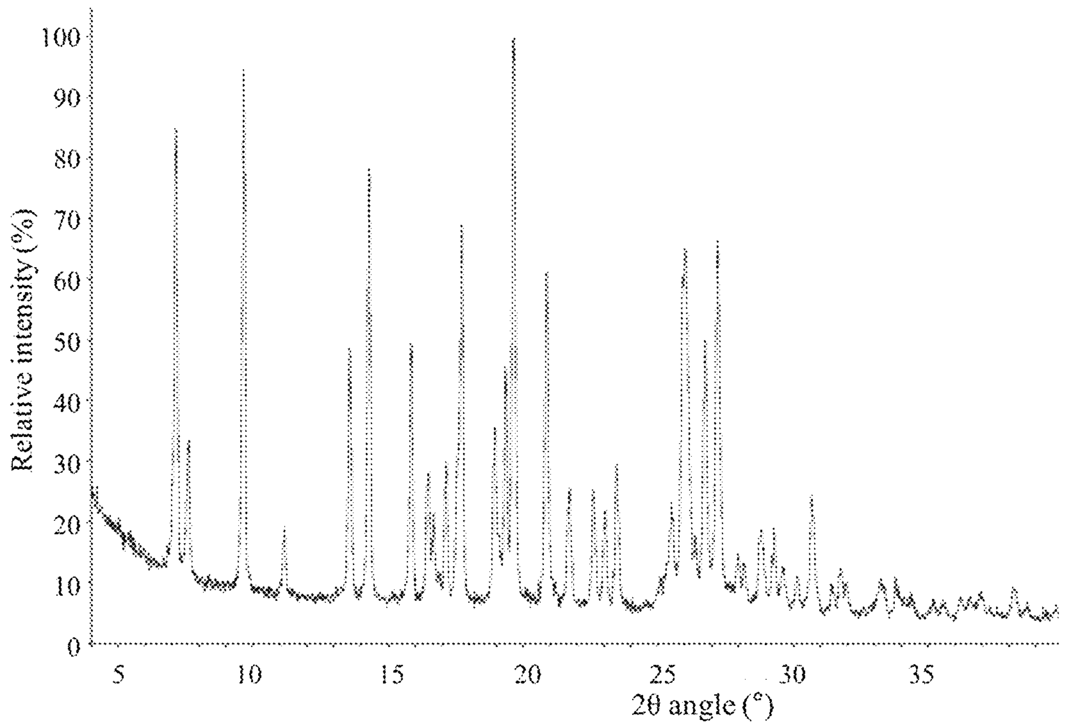
FIG. 1 is an XRPD pattern of the crystal form A of the compound of formula (I) measured by Cu-Kα radiation.

In order to better understand the content of the present disclosure, a further description will be given below in conjunction with specific embodiments, but the specific embodiments are not a limitation on the content of the present disclosure.

Embodiment 1: Preparation of Compound D

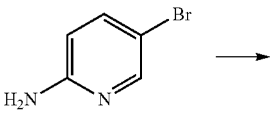

A

-continued

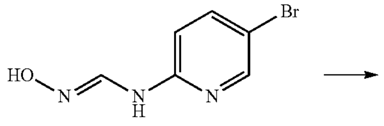

B

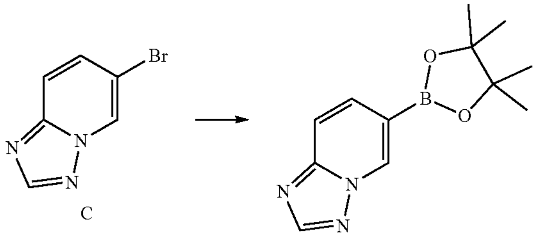

C

D

Step 1

To 50 L of kettle R1 were added 20 L of isopropanol, the material A (10 Kg. 1.0 eq) and N, N-dimethylformamide dimethyl acetal (8.53 Kg, 1.2 eq). The reaction solution was heated to 70-80° C. and stirred for 3 h. A sample were taken for detection, and the material A was disappeared. The reaction mixture was cooled to 70° C. and hydroxylamine hydrochloride (4.8 Kg, 1.2 eq) was added in batches while the internal temperature was controlled ≤80° C. After the addition was completed, the internal temperature was kept at 70-80° C. and stirred for 1 h. The sample was taken for detection and the reaction was completed. Heating was stopped, the reaction solution was cooled to room temperature and filtered. The filter cake was washed with 2 L of isopropanol and dried under reduced pressure and vacuum to obtain compound B.

LCMS: m/z: 217.7 $[M+1]^+$;

$^1$H NMR (400 MHz, MeOD-$d_4$): δ 8.24 (d, J=2.4 Hz, 1H), 7.90 (s, 2H), 7.76 (dd, J=8.8, 2.4 Hz, 1H), 6.89 (d, J=8.8 Hz, 1H).

Step 2

To 50 L of kettle R1 were added 22.4 L of isopropyl acetate and the compound B (4.48 Kg, 1.0 eq). The reaction system was cooled to 0-10° C. and trifluoroacetic anhydride (6.2 Kg, 1.5 eq) was added dropwise while the internal temperature was controlled at 0-10° C. After the addition was completed, refrigeration was turned off, the reaction solution was slowly warmed to room temperature and stirred for 16 h. A sample was taken for detection and the reaction was completed. 2.44 kg of sodium hydroxide was weighed and mixed with 30 L of ice evenly. The reaction solution was poured into the above solution in batches. The mixture was stirred for 0.2 h and filtered. The filter cake was washed with 1 L of isopropyl acetate. The filtrate was separated and the aqueous phase was extracted twice with 5 L of isopropyl acetate each time. The organic phases were combined and washed with 10 L of water. The organic phase was separated and concentrated to obtain the crude product. The crude product and the filter cake were combined, and the combined solid was slurried at 16-22° C. for 2 h. The suspension was filtered, and the filter cake was washed with 2 L of the above mixed solvents. The solid was collected and dried under reduced pressure and vacuum to obtain compound C.

LCMS: m/z: 199.7 $[M+1]^+$;

$^1$H NMR (400 MHz, deuterated chloroform): δ 8.77 (s, 1H), 8.34 (s, 1H), 7.70-7.60 (m, 2H).

Step 3

To 50 L of kettle R1 were added 30 L of dioxane, compound C (3.0 Kg, 1.0 eq), bis(pinacolato)diboron (3.85 Kg, 1.0 eq), potassium acetate (2.3 Kg, 1.5 eq) and Pd(dppf)$Cl_2$ (537 g, 0.05 eq). The kettle R1 was evacuated and purged with nitrogen four times. The temperature was controlled at 85-105° C. and the mixture was stirred for 18 h. A sample was taken for detection and the mixture was cooled to room temperature, filtered through diatomite and the filter cake was washed with dioxane. The combined organic phase was concentrated under reduced pressure to obtain the residue. 2.5 L of isopropyl acetate was added to R1, the residue was transferred to kettle R1, diatomite was added thereto, then n-heptane was added thereto, and the mixture was heated to 100° C. and stirred for 16 h. The mixture was cooled to room temperature, filtered through diatomite. The filter cake was washed with n-heptane, and the combined organic phase was spin-dried to obtain the crude product. The crude product was slurried with n-heptane at room temperature for 16 h. The suspension was filtered and the filter cake was washed with n-heptane. The filter cake was dried to obtain compound D.

LCMS: m/z: 246.2[M+1]$^+$;

$^1$H NMR (400 MHz, deuterated chloroform): δ 8.90 (s, 1H), 8.29 (s, 1H), 7.76-7.66 (m, 2H), 1.30 (s, 12H).

Embodiment 2: Preparation of the Compound of Formula (I)

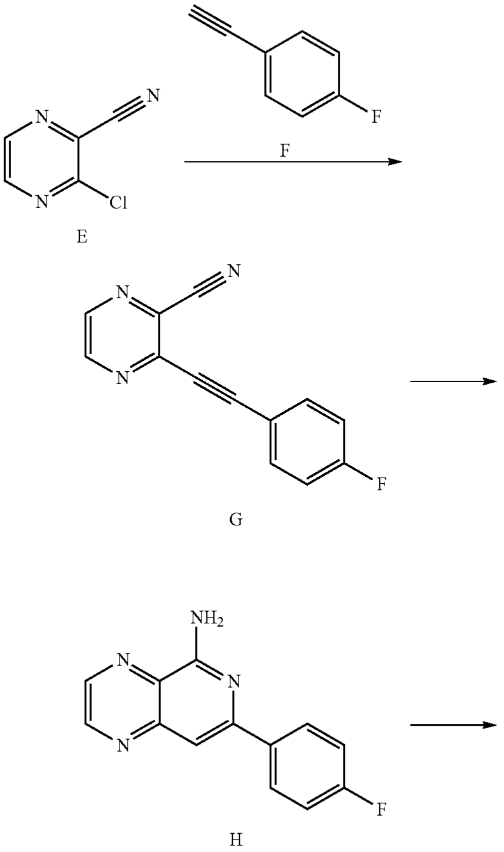

E

G

H

-continued

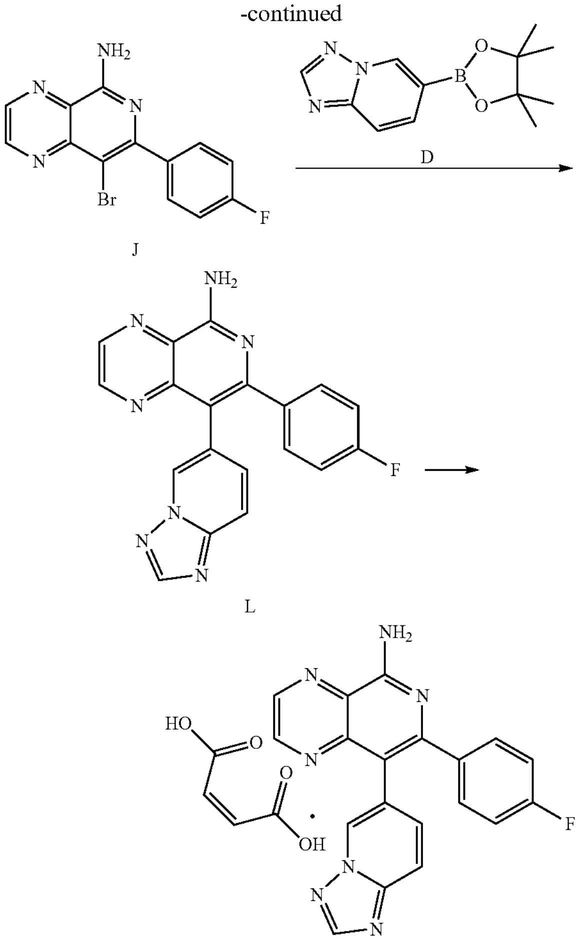

J

L (I)

Step 1

To 50 L of kettle was added 24 L of DMF and stirring was started. Compound E (5.0 Kg, 1.0 eq), compound F (4304.14 g, 1.0 eq), cuprous iodide (66.88 g, 0.01 eq) and triethylamine (5330.00 g, 1.5 eq) were added to the kettle, and then the mouth of the kettle was washed with 0.95 kg DMF. $Pd(PPh_3)_2Cl_2$(123.24 g, 0.005 eq) was added to the kettle without replacing nitrogen. The internal temperature was kept below 50° C., and the mixture was stirred for 16 h. A sample was taken for detection and the reaction mixture was directly filtered. Every ⅕ of the filtrate was slowly added to 25 L of water and kept stirring for 0.5 h. The operation was repeated five times to process all the filtrate. The mixed solution was filtered to obtain 9.82 kg of crude product. The crude product was slurried with 14 L of ethanol at room temperature and then the slurry was filtered. The filter cake was dried under reduced pressure in a vacuum drying oven to obtain compound G.

LCMS: m/z: 223.6 [M+1]$^+$;

$^1$H NMR (400 MHz, deuterated chloroform): δ 8.76 (d, J=1.6 Hz, 1H), 8.60 (d, J=2.4 Hz, 1H), 7.73-7.65 (m, 2H), 7.13 (t, J=8.4 Hz, 2H).

Step 2

To 50 L of kettle was added 23 L of DMF and stirring was started. Compound G (7700.00 g, 1.0 eq), ammonium acetate (4945.45 g, 2.0 eq) and copper trifluoromethanesulfonate (232.07 g, 0.02 eq) were added, and then the mouth of the kettle was washed with 1 L of DMF. Then heating was started and the internal temperature was kept at 100° C., and the mixture was stirred for 16 h. A sample was taken for detection and the reaction solution was directly filtered. The solid was collected as a crude product with a crude product of 6.98 kg. The crude product was slurried at room temperature with 14 L of water and then the slurry was filtered. Then the crude product was slurried with 14 L of ethanol at reflux, and then the slurry was filtered. The filter cake was dried under reduced pressure in a vacuum drying oven to obtain compound H.

LCMS: m/z: 241.0 $[M+1]^+$;

$^1$H NMR (400 MHz, DMSO-$d_6$): δ 9.44 (d, J=2.0 Hz, 1H), 9.19 (d, J=2.0 Hz, 1H), 8.73 (dd, J=8.8, 3.2 Hz, 2H), 8.06 (s, 1H), 7.71 (t, J=8.8 Hz, 2H), 7.29 (br, 2H).

Step 3

To 50 L of kettle was added 10.6 L of DMF and stirring was started. Compound H (5.30 kg, 1.0 eq) and N-Bromosuccinimide (4.66 kg, 1.2 eq) were added in batches while the internal temperature was kept <50° C. during addition. Then heating was started and the internal temperature was kept at 50° C., and the mixture was stirred for 2 h. A sample was taken for detection and 20 L of EtOAc was added to the reaction solution. The internal temperature was kept at 50° C., and the mixture was stirred for 0.5 h. The reaction mixture was cooled to room temperature and then filtered. The crude product was slurried with 16 L of THF at reflux. The slurry was filtered, and the filter cake was dried under reduced pressure in a vacuum drying oven to obtain compound J.

LCMS: m/z: 320.9 $[M+1]^+$;

$^1$H NMR (400 MHz, DMSO-$d_6$): δ 9.16 (d, J=1.6 Hz, 1H), 8.89 (d, J=2.0 Hz, 1H), 7.72 (dd, J=8.8, 6.0 Hz, 2H), 7.64 (br, 2H), 7.32 (t, J=8.8 Hz, 2H).

Step 4

To 50 L of kettle A were added 22 L of THF, compound J (4.4 kg, 1.0 eq), $P_3KO_4$ (7991.97 g, 3.0 eq), compound D (6.15 kg, 1.38 eq), Pd(dtbpf)$_2$Cl$_2$ (408.97 g, 0.05 eq) and 4.4 L of $H_2O$. Stirring was started and the kettle was evacuated and purged with nitrogen three times. The temperature was controlled at 70° C. and stirred for 16 h. A sample was taken for detection and the reaction solution was concentrated under reduced pressure, 33 L of DCM and 10 L of EtOH were added to the kettle. Then the mixture was stirred at 30° C. for 0.5 h, the concentrate was added with 4.4 L of EtOAc, the temperature was controlled at 60° C., and the mixture was stirred for 1 h, cooled to room temperature and filtered. The filter cake was diluted with 8.8 L of water and then stirred at 25° C. for 1 h. The suspension was filtered and the filter cake was diluted with 4.4 L of DMF, the temperature was controlled at 50° C., and the mixture was stirred for 0.5 h, 22 L of ethyl acetate was added, then the temperature was controlled at 50° C., and the mixture was stirred for 1 h. Then the mixture was cooled to room temperature, filtered, the filter cake was diluted with 36.7 L of DCM and 9.7 L of EtOH. The mixture was warmed to 40° C. and 1,3,5-triazine-2,4,6-trimercaptan trisodium (0.88 kg) was added. The temperature was controlled at 40° C. and the mixture was stirred for 15 h and then filtered. The operation was repeated three times, filtered and the filtrate was spin-dried to obtain compound L.

LCMS: m/z: 358.1 $[M+1]^+$.

Step 5

To 50 L kettle A were added 24.2 L of THF, then compound L (490 g, 1.0 eq) was added to kettle C. The temperature was controlled at 50° C. and the mixture was stirred for 1 h and then filtered. To 50 L kettle A was added the filtrate, and then a solution of maleic acid (165.98 g, 1.05 eq) dissolved in 29 L of THF was added to kettle C, the temperature was controlled at 50° C. and the mixture was stirred for 14 h and then cooled to room temperature 20-25° C. and directly filtered. The filter cake was slurried with 1.32 L of ethanol at room temperature for 16 h. The slurry was filtered and the filter cake was dried under reduced pressure in a vacuum drying oven to obtain the crystal form A of the compound of formula (I).

LCMS: m/z: 358.1 $[M+1]^+$;

$^1$H NMR (400 MHz, DMSO-$d_6$): δ 9.02 (d, J=2.0 Hz, 1H), 8.88 (d, J=2.0 Hz, 1H), 8.79 (d, J=1.6 Hz, 1H), 8.48 (s, 1H), 7.77 (d, J=0.8 Hz, 1H), 7.75 (br, 2H), 7.47-7.43 (m, 3H), 7.14 (t, J=4.6 Hz, 2H), 6.27 (t, J=10.8 Hz, 2H).

Embodiment 3

According to Table 7, the crystal form A of the compound of formula (I) was weighed into liquid phase vials, and then solvents or mixed solvents in Table 7 were added to form a suspension, respectively. The above suspension samples were placed on a constant temperature mixer at 40° C. and shaken at 700 rpm for 2 days. Then the solid was separated by centrifugation (centrifuge 8000 rpm, for three minutes) and dried overnight in a vacuum drying oven at 30° C. to obtain the crystal form A of the compound of formula (I).

TABLE 7

Solution suspension crystallization method for screening polycrystalline forms of maleates

| Number | Solvent | Amount (mg) added | Volume (mL) added |
|---|---|---|---|
| 1 | methanol | 47.978 | 1.0 |
| 2 | Ethanol | 48.198 | 1.0 |
| 3 | Acetonitrile | 49.372 | 1.0 |
| 4 | Acetone | 48.064 | 1.0 |
| 5 | Ethyl acetate | 47.560 | 1.0 |
| 6 | Tert-butyl methyl ether | 51.680 | 1.0 |
| 7 | Tetrahydrofuran | 52.992 | 1.0 |
| 8 | Water | 48.718 | 1.0 |
| 9 | Methanol-water (1:1) | 49.108 | 1.0 |
| 10 | Acetonitrile-water (1:1) | 52.343 | 1.0 |

Embodiment 4: Preparation of the Compound of Formula (II-1)

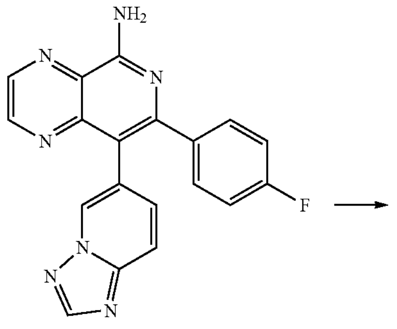

L

-continued

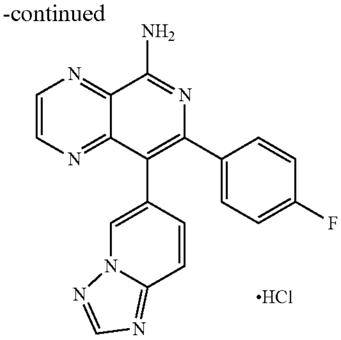

(II-1)

At 25° C., to the reaction bottle were added 200 mL of acetonitrile, 200 mL of water and compound L (6 g), the mixture was adjusted to pH=3-5 with 1M dilute HCl. And then the reaction solution was stirred at 25° C. for 0.5 h to obtain the compound of formula (II-1).

LCMS m/z: 358.2 $[M+H]^+$ $^1$H NMR (400 MHz, DMSO-$d_6$) δ=9.24 (t, J=3.6 Hz, 1H), 9.12 (d, J=2.0 Hz, 1H), 8.87 (s, 1H), 8.59 (t, J=5.2 Hz, 1H), 7.84 (t, J=8.4 Hz, 1H), 7.58-7.55 (m, 2H), 7.50(d, J=15.6 Hz, 1H), 7.27 (t, J=9.2 Hz, 2H).

Embodiment 5: Preparation of the Crystal Form B of the Compound of Formula (II)

About 100 mg of compound L was weighed at room temperature and added to a 40 mL of flask, and 30 mL of acetone was added to dissolve compound L, and then 24.17 μL of HCl (the molar ratio of compound L:hydrochloric acid was 1:1.05) was slowly added. The sample was placed on a magnetic stirrer (40° C.) and stirred for one day to obtain the crystal form B of the compound of formula (II).

Embodiment 6: Preparation of the Crystal Form C of the Compound of Formula (III)

(III)

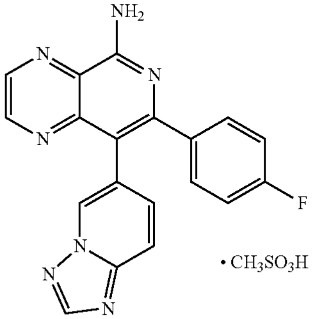

About 100 mg of compound L was weighed at room temperature and added to a 40 mL of flask, and 30 mL of acetone was added to dissolve compound L, and then 19.08 μL of methanesulfonic acid (the molar ratio of compound L:methanesulfonic acid was 1:1.05) was slowly added. The sample was placed on a magnetic stirrer (40° C.) and stirred for one day to obtain the crystal form C of the compound of formula (III).

Embodiment 7: Preparation of the Crystal Form D of the Compound of Formula (IV)

(IV)

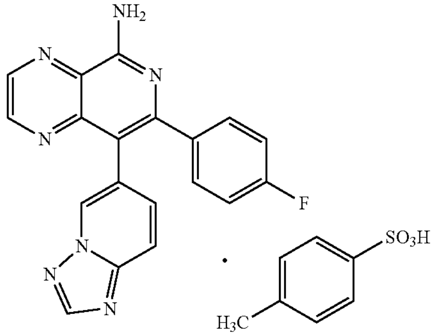

About 100 mg of compound L was weighed at room temperature and added to a 40 mL of flask, and 30 mL of acetone was added to dissolve compound L, and then 200.57 μL of p-toluenesulfonic acid (the molar ratio of compound L:p-toluenesulfonic acid was 1:1.05) was slowly added. The sample was placed on a magnetic stirrer (40° C.) and stirred for one day to obtain the crystal form D of the compound of formula (IV).

Embodiment 8: Preparation of the Crystal Form E of the Compound of Formula (V)

(V)

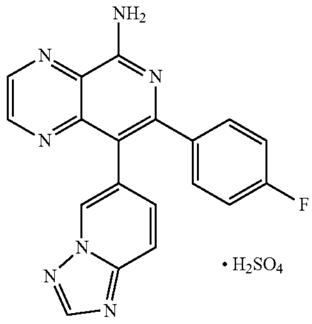

About 100 mg of compound L was weighed at room temperature and added to a 40 mL of flask, and 30 mL of acetone was added to dissolve compound L, and then 15.99 μL of sulfuric acid (the molar ratio of compound L:sulfuric acid was 1:1.05) was slowly added. The sample was placed on a magnetic stirrer (40° C.) and stirred for one day to obtain the crystal form E of the compound of formula (V).

Embodiment 9: Stability Experiments of Crystal Forms

A certain amount (approximately 10 mg) of two parts of the crystal form A of the compound of formula (I), the crystal form B of the compound of formula (II) and the crystal form C of the compound of formula (III) were weighed in parallel, and added to a 40 mL of sample bottle, which were placed in a constant temperature and humidity box at 60° C./75% humidity for 1 week. Another sample (about 10 mg) of the crystal form A of the compound of formula (I), the crystal form B of the compound of formula (II) and the crystal form C of the compound of formula (III) were placed in a refrigerator at −20° C. as control samples. At the time point of investigation, the corresponding test sample was taken out of the stability box, the aluminum foil paper was removed from the sample bottle of 60° C./75% RH, and the sample bottle was covered with a bottle cap. The 0-day samples were taken out of the refrigerator and analyzed after the samples were restored to room temperature. The experimental results were shown in Table 8.

TABLE 8

Experimental results of stability of crystal forms

| | Relative retention time | 0.36 | 0.45 | 0.49 | 0.67 | 0.70 | 1.18 | Total impurities % |
|---|---|---|---|---|---|---|---|---|
| Crystal form A of the compound of formula (I) | 0 day | 0.06 | 0.09 | 0.09 | 0.05 | 0.11 | 0.29 | 0.69 |
| | 60 C./75% RH_one week | 0.05 | 0.09 | 0.09 | 0.05 | 0.12 | 0.29 | 0.69 |
| Crystal form B of the compound of formula (II) | 0 day | 0.09 | 0.10 | 0.09 | 0.05 | 0.15 | 0.40 | 0.87 |
| | 60 C./75% RH_one week | 0.09 | 0.10 | 0.09 | 0.05 | 0.15 | 0.40 | 0.87 |
| Crystal form C of the compound of formula (III) | 0 day | 0.05 | 0.09 | 0.08 | 0.04 | 0.09 | 0.50 | 0.96 |
| | 60 C./75% RH_one week | 0.05 | 0.09 | 0.08 | 0.04 | 0.09 | 0.52 | 1.16 |

Conclusion: The crystal form A of the compound of formula (I), the crystal form B of the compound of formula (II) and the crystal form C of the compound of formula (III) have good stability under high temperature and high humidity conditions.

Experimental Embodiment 1: In Vitro Activity Test Experiment of the Compound of the Present Disclosure Test Experiment of Calcium Current of Human Adenosine $A_{2A}$ Receptor Cell source:

The $A_{2A}$ stable cell line was constructed by Shanghai WuXi AppTec, the host cell was CHO.

Detection kit:

Fluo-4 Direct kit, (Invitrogen, catalog number F10471). After the fluorescence detection reagent in the kit (which specifically binds to calcium ions and causes an increase in fluorescence signal) was incubated with the cells for an appropriate period of time, the compound was added to stimulate the cells to cause changes in intracellular calcium flow, thereby causing changes in fluorescence signals, which can reflect the strength of the agonistic or inhibitory activity of the compound.

Cell culture medium:

F12+10% Fetal Bovine Serum+Geneticin 300 μg/mL+Blasticidin 2 μg/mL

Compound dilution buffer:

Hanks balanced salt buffer (Invitrogen)+20 mM HEPES, configure before each use

Agonist:

NECA (Sigma-E2387)

Reference compound (antagonist):

CGS-15943 (Sigma-C199)

Compound dilution:

The test compound was dissolved in DMSO to prepare a 10 mM stock solution. The test compound was diluted with DMSO to 0.2 mM, and the reference compound CGS-15943 was diluted with DMSO to 0.015 mM. Then 10-point 3-fold serial dilution was performed with ECHO. Then the dilution was transferred 900 nL to the compound plate (Greiner-781280), and 30 μL of compound dilution buffer was added thereto. The final initial concentration of the test compound was 1 μM, and the CGS-15943 was 0.075 μM.

Test methods:

Cell preparation:

The cryopreserved $A_{2A}$ cells were resuscitated and were resuspend in culture medium to $1\times10^6$ cells/mL, and inoculated 384-well polylysine-coated cell plate (Greiner-781946) with 20 μL/well, and incubated overnight at 37° C. in a 5% $CO_2$ incubator.

The cell plate prepared the day before was taken out from the incubator, 20 μL of 2×Fluo-4Direct™ buffer was added to each well, and incubated for 50 minutes at 37° C. in a 5% $CO_2$ incubator, and placed at room temperature for 10 minutes.

$EC_{80}$ determination of agonist NECA:

Dilution of agonist NECA: 10-point 3-fold serial dilution of NECA with an initial concentration of 0.15 mM was performed with ECHO, then the dilution was transferred 900 nL to the corresponding compound plate; then 30 μL of compound dilution buffer was added to the corresponding compound plate. The final initial concentration was 750 nM. The FLIPR instrument software was run, according to the set procedure, 10 μL of compound dilution buffer was added to the cell plate, and the fluorescence signal was read. Then 10 μL of the agonist reference compound of a predetermined concentration was added to the cell plate, and the fluorescence signal was read. After reading, the data was exported through the "Max-Min" and "Read 90 to Maximum allowed" methods in the software, the EC80 of the $A_{2A}$ cell line was calculated, and an agonist with a concentration of $6\times EC_{80}$ was prepared. The reference compound agonist with the corresponding cell concentration of $6\times EC_{80}$ with buffer salt solution was prepared, and was added 30 μL/well to the corresponding compound plate for later use.

$IC_{50}$ determination of the test compound:

The FLIPR instrument software was run, according to the set procedure, 10 μL of the test compound and reference compound of a predetermined concentration were added to the cell plate, and the fluorescence signal was read. Then 10

μL of the reference compound agonist at a concentration of $6\times EC_{80}$ was added to the cell plate, and the fluorescence signal was read. For agonist detection of compounds, the data was exported through the "Max-Min" and "Read 1 to 90" methods in the software. For antagonist detection of compounds, the data was exported through the "Max-Min" and "Read 90 to Maximum allowed" methods in the software. The data was analyzed with GraphPad Prism 5.0 to calculate the $IC_{50}$ value of the test compounds. The test results were shown in Table 9.

TABLE 9

Results of in vitro screening experiments for the compound of the present disclosure

| Test sample | $IC_{50}$ vaue (nM) |
|---|---|
| Compound of formula (II-1) | 1.14 |

Conclusion: The compound of the present disclosure exhibits excellent adenosine $A_{2A}$ receptor antagonistic activity.

Experimental Embodiment 2: Pharmacokinetic Experiment of the Compound of the Present Disclosure Experimental materials: Balb/c mice (female, 15-30 g, 7-9 weeks old, Shanghai Lingchang) were used.

Experimental method: The rodent pharmacokinetic characteristics of the compound after intravenous injection and oral administration were tested by a standard protocol. In the experiment, the candidate compound was formulated into a clear solution and given to mice by a single intravenous injection and a single oral administration. The solvent for intravenous injection (IV) was a mixed solvent of 5% DMSO/5% polyethylene glycol hydroxystearate/90% water, and the solvent for oral (PO) was a mixed solvents of 1% tween80, 9% PEG400, 90% $H_2O$ (pH=3). Whole blood samples within 48 hours were collected, centrifuged at 3000 g for 15 minutes at 4 degrees, separated the supernatant to obtain a plasma sample. Then 20 times the volume of acetonitrile solution containing internal standard was added to precipitate the protein, the mixture was centrifuged to take the supernatant, equal volume of water was added and centrifuge to take the supernatant again for injection. The blood drug concentration was quantitatively analyzed by LC-MS/MS analysis method, and the pharmacokinetic parameters were calculated, such as peak concentration, peak time, clearance rate, half-life, area under the drug-time curve, bioavailability, etc. The test results were shown in Table 10.

TABLE 10

PK parameters in plasma of embodiment compounds

| Test sample | Clearance rate (mL/min/kg) | Half life $T_{1/2}$ (h) | Concentration integral AUC (nM · hr) | Bioavailability F (%) |
|---|---|---|---|---|
| Compound of formula (II-1) | 5.87 | 0.82 | 24050 | 30.4 |

Conclusion: The compound of the present disclosure can significantly improve the pharmacokinetic index of mice.

Experimental Embodiment 3: In Vivo Drug Efficacy Experiment of the Compound of the Present Disclosure Experimental materials: BALB/c mice (female); mouse colon cancer CT26 cells (cell bank of the Type Culture Collection Committee of the Chinese Academy of Sciences), were cultured in a monolayer in vitro, and the culture condition was RPMI-1640 medium containing 10% fetal bovine serum, and cultured in 5% $CO_2$ incubator at 37° C. Trypsin-EDTA was used for conventional digestion and passage. When the cells were in the exponential growth phase and the saturation was 80%-90%, the cells were collected and counted.

Compound preparation: The compound of formula (II-1) was weighed and added to a solvent (10% PEG400+90% (10% Cremophor aqueous solution)) to prepare samples of 2.5 mg/mL, 5 mg/mL, and 10 mg/mL, respectively. 72 μL of CS1003 (PD-1 antibody) solution (25 mg/mL) was taken and added with 1.728 mL of Dulbecco's Phosphate Buffer Saline (DPBS) to prepare a solution of 1 mg/mL, then added with 16.2 ml DPBS to prepare a clear solution of 0.1 mg/mL.

Experimental operation: The cells in Dulbecco's phosphate buffer were resuspended at a density of $3\times10^6$ cells/mL. 0.1 mL of DPBS (containing $3\times10^5$ CT26 cells) was subcutaneously inoculated on the right back of each mouse. On the day of inoculation, the mice were randomly divided into groups according to their body weight with 9 mice in each group, and the administration was started for 20 days. During the entire experiment, the animals were weighed and monitored daily. If there were special circumstances, the relevant project leader should be notified in time and corresponding records should be made. The tumor diameter was measured with vernier calipers twice a week. The dosage regimen was shown in Table 11. The calculation formula of tumor volume was: $V=0.5\times a\times b^2$, where a and b represent the long diameter and short diameter of the tumor, respectively.

TABLE 11

Dosage regimen for in vivo drug efficacy experiments of the compounds of the present disclosure

| Group | Test sample | Administration route | Dosage (mg/kg) | Administration volume (mL/kg) | Dosage regimen |
|---|---|---|---|---|---|
| 1 | Solvent control | Gavage administration | — | 10 | Once a day |
| 2 | C51003 | Intraperitoneal injection | 1 | 10 | Day 7.10, 13, 16 |
| 3 | Compound of formula (II-1) | Gavage administration | 100 | 10 | Once a day |

TABLE 11-continued

| Dosage regimen for in vivo drug efficacy experiments of the compounds of the present disclosure | | | | | |
|---|---|---|---|---|---|
| Group | Test sample | Administration route | Dosage (mg/kg) | Administration volume (mL/kg) | Dosage regimen |
| 4 | Compound of formula (II-1) + (C51003) | Intraperitoneal injection + Gavage administration | 25 Compound of formula (II-1) + 1 (C51003) | 10 + 10 | Once a day + Day7.10, 13, 16 |
| 5 | Compound of formula (II-1) + (CS1003) | Intraperitoneal injection + Gavage administration | 50 Compound of formula (II-1) + 1 (CS1003) | 10 + 10 | Once a day + Day7.10, 13, 16 |
| 6 | Compound of formula (II-1) + (CS1003) | Intraperitoneal injection + Gavage administration | 100 Compound of formula (II-1) + 1 (CS1003) | 10 + 10 | Once a day + Day7.10, 13, 16 |
| 7 | Compound of formula (II-1) | Gavage administration | 50 | 10 | Twice a day |
| 8 | Compound of formula (II-1) + (CS1003) | Intraperitoneal injection + Gavage administration | 50 Compound of formula (II-1) + 1 (CS1003) | 10 + 10 | Twice a day + Day7.10, 13, 16 |

The anti-tumor efficacy of the compound was evaluated by GI (%) or relative tumor proliferation rate T/C (%). Relative tumor proliferation rate T/C (%)=Vt/Vc×100% (Vt: average tumor volume in the treatment group; Vc: average tumor volume in the negative control group). Vt and Vc are taken from the same day data.

GI (%), tumor inhibition rate. GI(%)=1−Vt/Vc×100%.

The statistical analysis was based on the relative tumor volume and tumor weight at the end of the experiment using SPSS software. The comparison between the two groups was analyzed by t-test, and the comparison between three or more groups was analyzed by one-way ANOVA. If the variance was uniform (F values were not significantly different), the analysis should be performed by Tukey's method. If the variance was not uniform (F Values were significantly different), Games-Howell method was used to test. P<0.05 was considered a significant difference.

On the 20th day after the start of administration, the tumor volume in the solvent group reached 847.09±79.65 $mm^3$, and the tumor volume in the CS1003 (1 mg/kg) group was 487.34±109.07 $mm^3$, and its tumor inhibition rate was 42.47% (no significant difference with the solvent control group). Compared with the solvent control group, each group of combination administration could significantly inhibit the growth of transplanted tumors in vivo, and the efficacy of the compound of formula (II-1) combined with CS1003 was positively correlated with its dosage and frequency of administration. The tumor volumes of 25 mg/kg, 50 mg/kg and 100 mg/kg compound of formula (II-1) combined with 1 mg/kg CS1003 at the experimental end point were 312.06±80.17 $mm^3$, 246.48±62.57 $mm^3$, and 233.10±59.55 $mm^3$, respectively; tumor inhibition rates were 63.16%, 70.90%, and 72.48% (P<0.001). The compound of formula (II-1) (50 mg/kg) administered twice a day combined with CS1003 showed a stronger anti-tumor effect. The average tumor volume of this group at the end of the experiment was 142.17±40.30 $mm^3$, and the tumor suppression rate was 83.22%. (P<0.001). It could be seen that when the compound of formula (II-1) was combined with CS1003 for preventive administration, it could significantly inhibit the growth of in vivo allograft tumors of mouse colon cancer cell CT26.

Conclusion: The combination of the compound of the present disclosure and CS1003 has a good anti-tumor effect, and the combination of the compound of the present disclosure and CS1003 has a synergistic effect. The combination of compound of formula (II-1) and CS1003 could enhance the anti-tumor effect. Wherein, the compound of formula (II-1) administered at 25 mg/kg, 50 mg/kg, 100 mg/kg once a day combined with CS1003 group, the tumor inhibition rates were 63%, 71% and 72%, respectively; the compound of formula (II-1) administered at 50 mg/kg twice a day combined with CS1003 group, the tumor inhibition rate of was 83% (P<0.001), which was significantly different from the compound of formula (II-1) (50 mg/kg, BID) or CS1003 alone (p values were 0.002, 0.003, respectively).

Experimental Embodiment 4: In Vivo PK Experiment of the Compound of the Present Disclosure Blood was collected and tissues were collected from each group of the experiment at different time points (0 h, 0.25 h, 0.5 h, 1 h, 2 h, 4 h, 8 h and 24 h) on day 20 of the administration of experimental embodiment 3. The pharmacokinetic parameters of each experimental group were shown in Table 12, and the biological ratios of the tumor tissue drug concentration and the corresponding blood sampling point tumor tissue drug concentration and plasma drug concentration of each experimental group were shown in Table 13.

TABLE 12

Pharmacokinetic parameters of each experimental group

| | Test sample | Compound of formula (II-1) | Compound of formula (II-1) | Compound of formula (II-1) | Compound of formula (II-1) | Compound of formula (II-1) | Compound of formula (II-1) |
|---|---|---|---|---|---|---|---|
| PK | Group | 4 | 5 | 6 | 3 | 7 | 8 |
| PO | Cmax (nM) | 32200 | 57200 | 132000 | 114000 | 30100 | 47100 |
| | Tmax (h) | 0.500 | 0.250 | 0.250 | 0.250 | 0.500 | 0.500 |
| | T½ (h) | 1.09 | 1.05 | 0.655 | 0.81 | NR | 1.59 |
| | $AUC_{0\text{-}last}$ (nM · h) | 23500 | 70600 | 125000 | 145000 | 42000 | 77900 |

Note:
NR means not obtained.

TABLE 13

The biological ratio of the tumor tissue drug concentration and the corresponding blood sampling point tumor tissue drug concentration and plasma drug concentration of each experimental group measured in the experiment

| Test sample | Compound of formula (II-1) | | Compound of formula (II-1) | | Compound of formula (II-1) | | Compound of formula (II-1) | | Compound of formula (II-1) | | Compound of formula (II-1) | |
|---|---|---|---|---|---|---|---|---|---|---|---|---|
| Group | 25 mpk 4 | | 50 mpk 5 | | 100 mpk 6 | | 100 mpk 3 | | 50 mpk 7 | | 50 mpk 8 | |
| Time point(h) | 1 | 4 | 1 | 4 | 1 | 4 | 1 | 4 | 1 | 4 | 1 | 4 |
| Tumor drug concentration (nM) | 3480 | 925 | 9960 | 1660 | 18700 | 3030 | 17500 | 10600 | 3690 | 901 | ND | 3020 |
| T/P* Ratio | 0.7 | 0.9 | 0.4 | 1.8 | 0.5 | 4.2 | 0.6 | 0.9 | 0.7 | 9.8 | ND | 36 |

Note:
ND means not detected.
T/P*Ratio means the ratio of the compound exposure in tumor tissue and plasma.

Conclusion: The compound of the present disclosure has sufficient exposure in plasma and tumor tissues.

What is claimed is:

1. A crystal form of the compound of formula (I), (I)

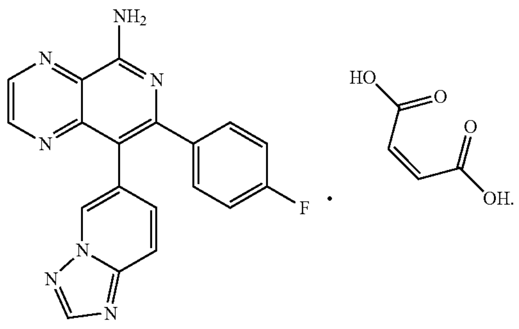

wherein an X-ray powder diffraction pattern thereof has characteristic diffraction peaks at the following 2θ angles: 7.16±0.2°, 9.66±0.2°, and 19.66±0.2°.

2. The crystal form of the compound of formula (I) according to claim 1, wherein the X-ray powder diffraction pattern thereof has additional characteristic diffraction peaks at the following 2θ angles: 13.59±0.2°, 14.30±0.2°, 15.87±0.2°, 17.73±0.2°, and 20.88±0.2°;

or, wherein a differential scanning calorimetry curve thereof has an onset of an endothermic peak at 205.67±3° C.;

or, wherein a thermogravimetric analysis curve thereof has a weight loss of 0.1846% at 120.00° C.±3° C.

3. The crystal form of the compound of formula (I) according to claim 2, wherein the X-ray powder diffraction pattern thereof has additional characteristic diffraction peaks at the following 2θ angles: 26.01±0.2°, 26.76±0.2°, and 27.21±0.2°.

Figure 2:
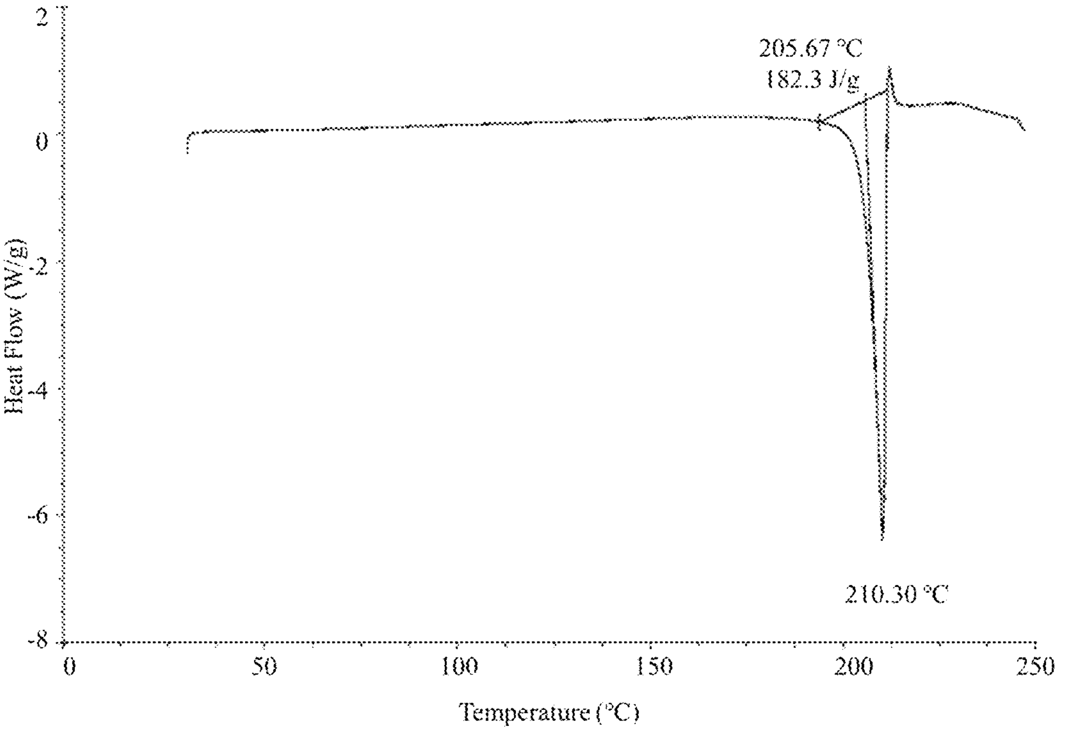
FIG. 2 is a DSC pattern of the crystal form A of the compound of formula (I)
Figure 3:
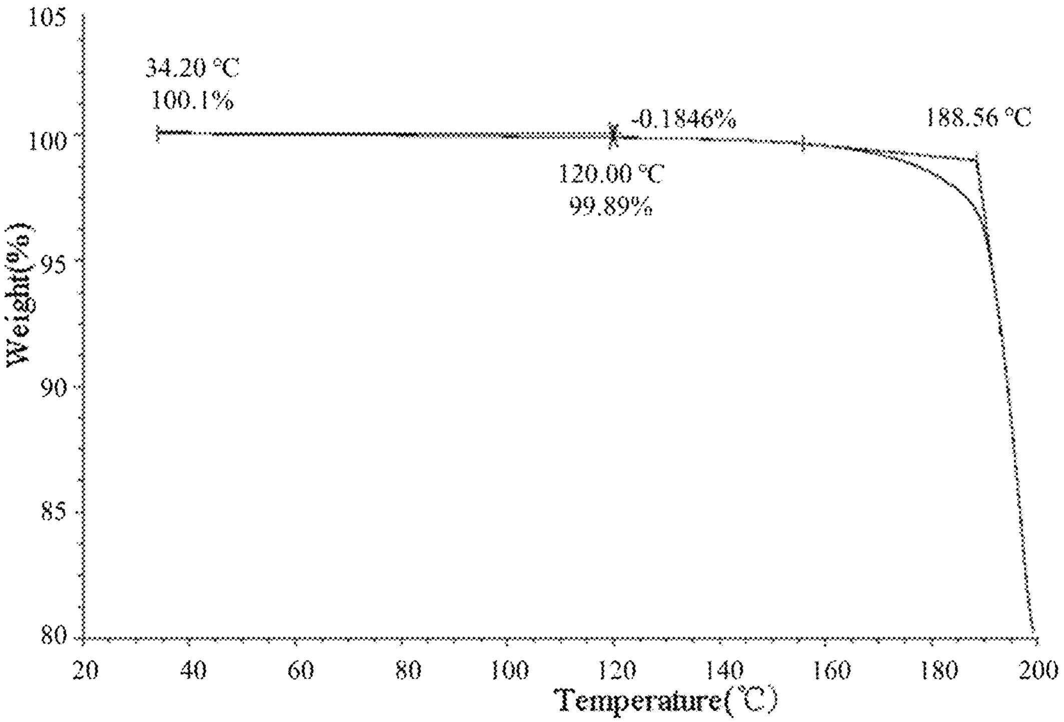
FIG. 3 is a TGA pattern of the crystal form A of the compound of formula (I)
Figure 4:
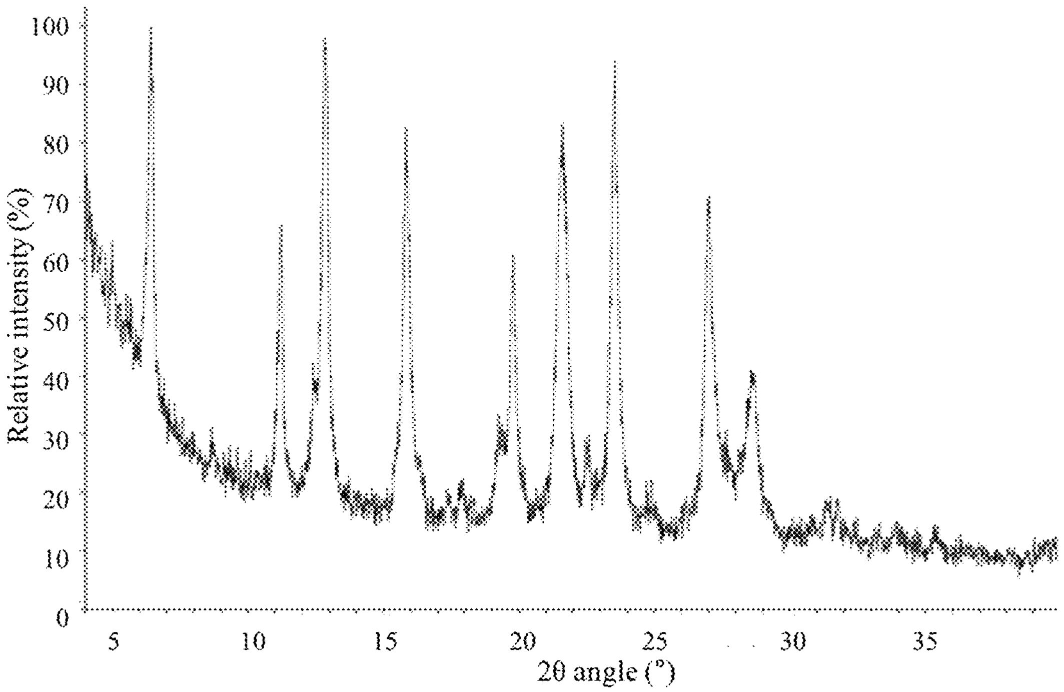
FIG. 4 is an XRPD pattern of the crystal form B of the compound of formula (II) measured by Cu-Kα radiation.
Figure 5:
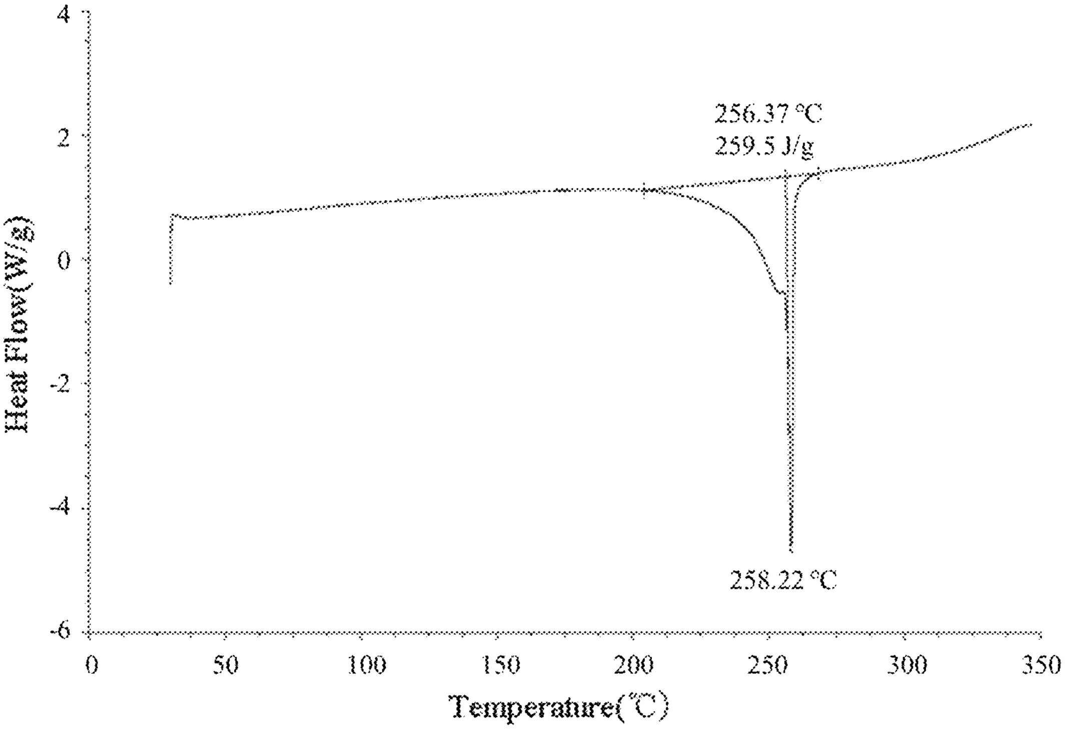
FIG. 5 is a DSC pattern of the crystal form B of the compound of formula (II)
Figure 6:
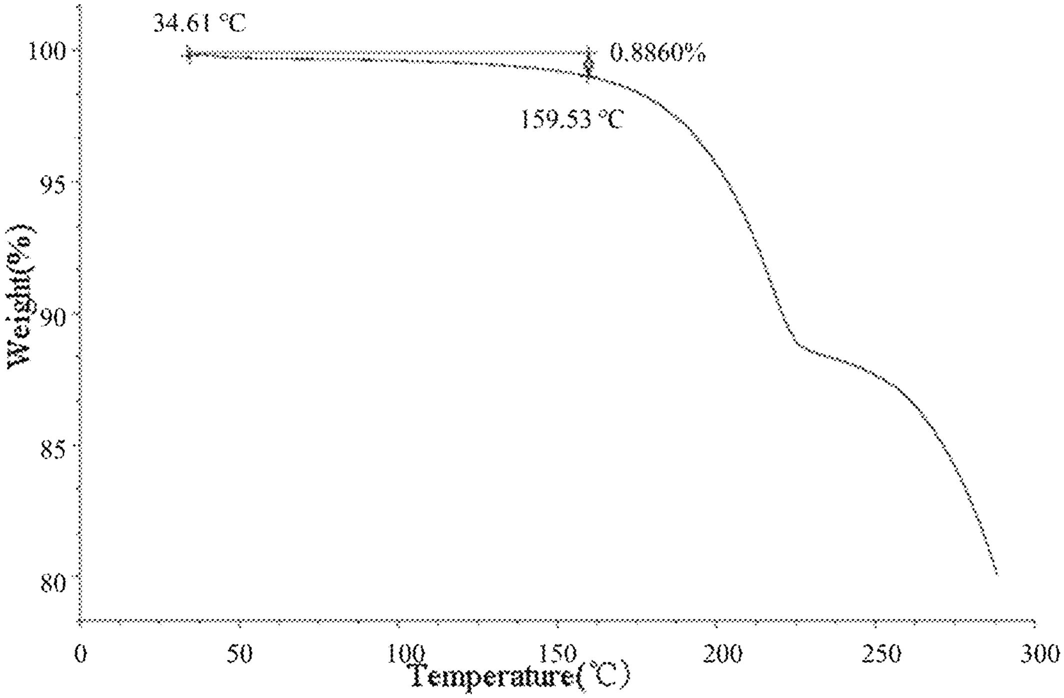
FIG. 6 is a TGA pattern of the crystal form B of the compound of formula (II)
Figure 7:
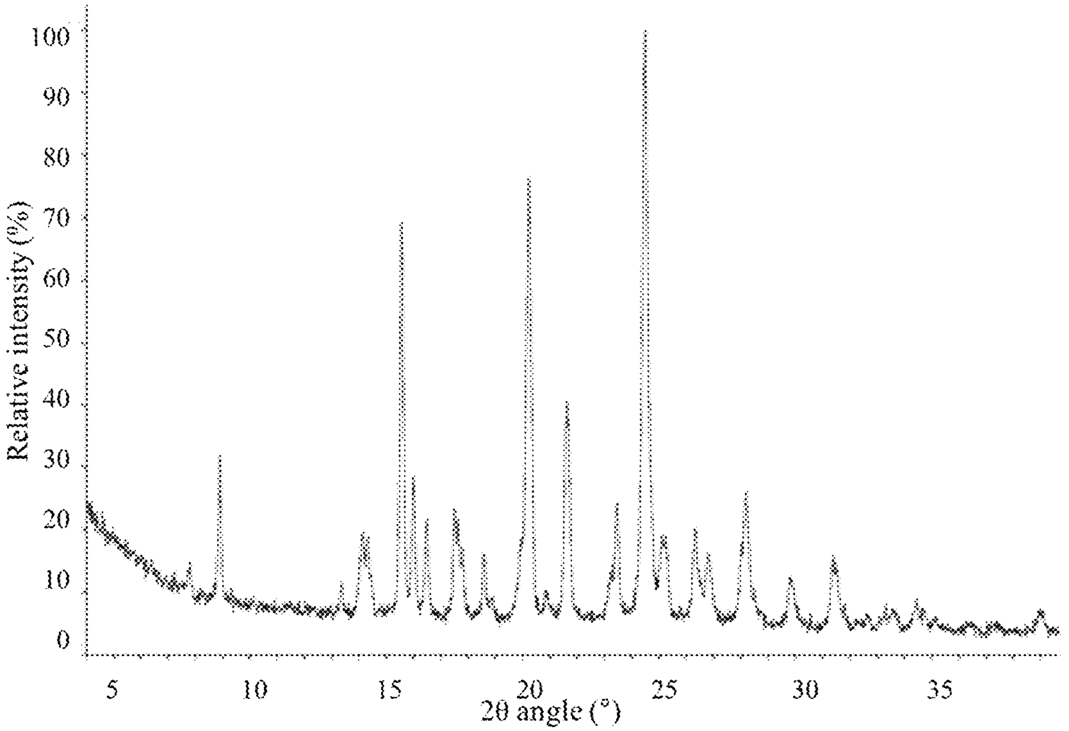
FIG. 7 is an XRPD pattern of the crystal form C of the compound of formula (III) measured by Cu-Kα radiation.
Figure 8:
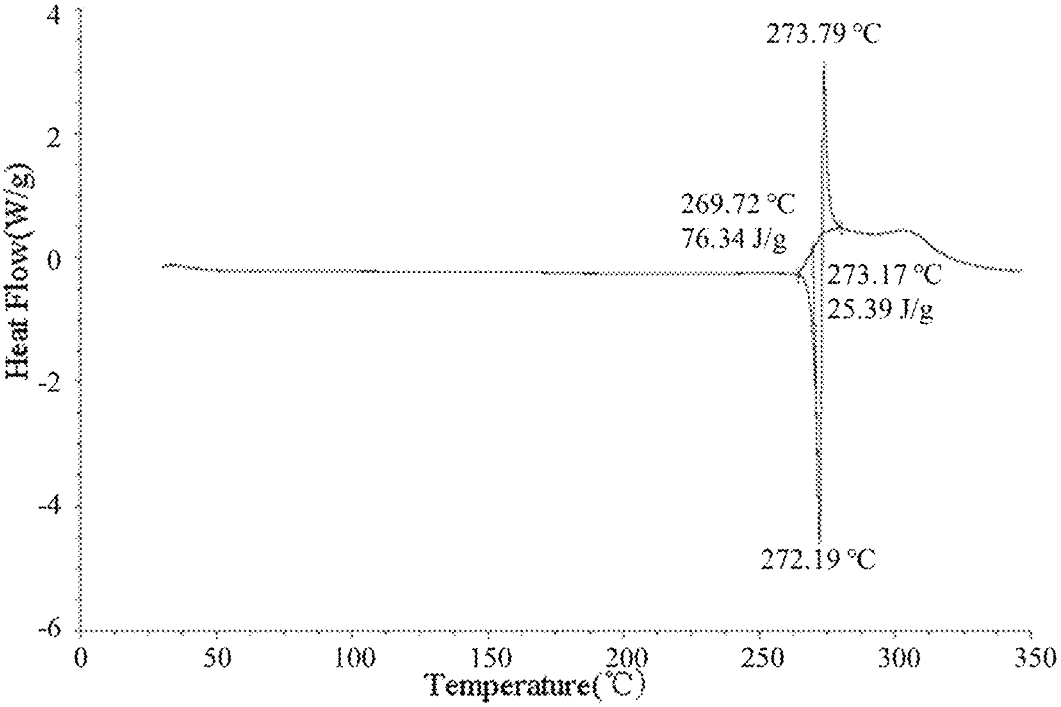
FIG. 8 is a DSC pattern of the crystal form C of the compound of formula (III)
Figure 9:
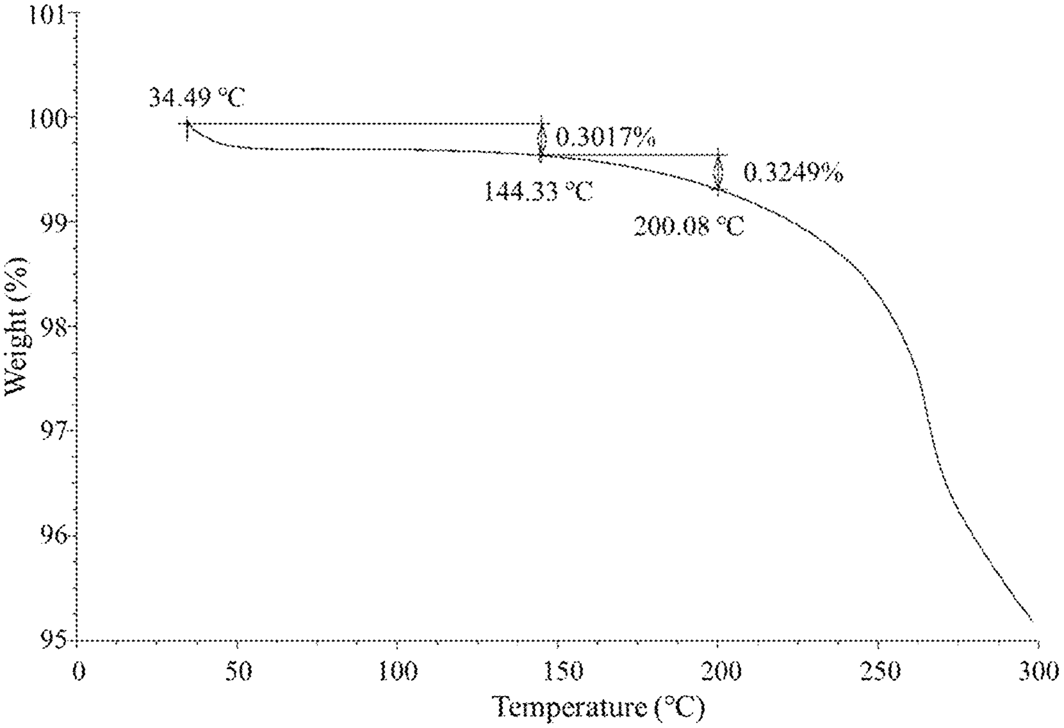
FIG. 9 is a TGA pattern of the crystal form C of the compound of formula (III)
Figure 10:
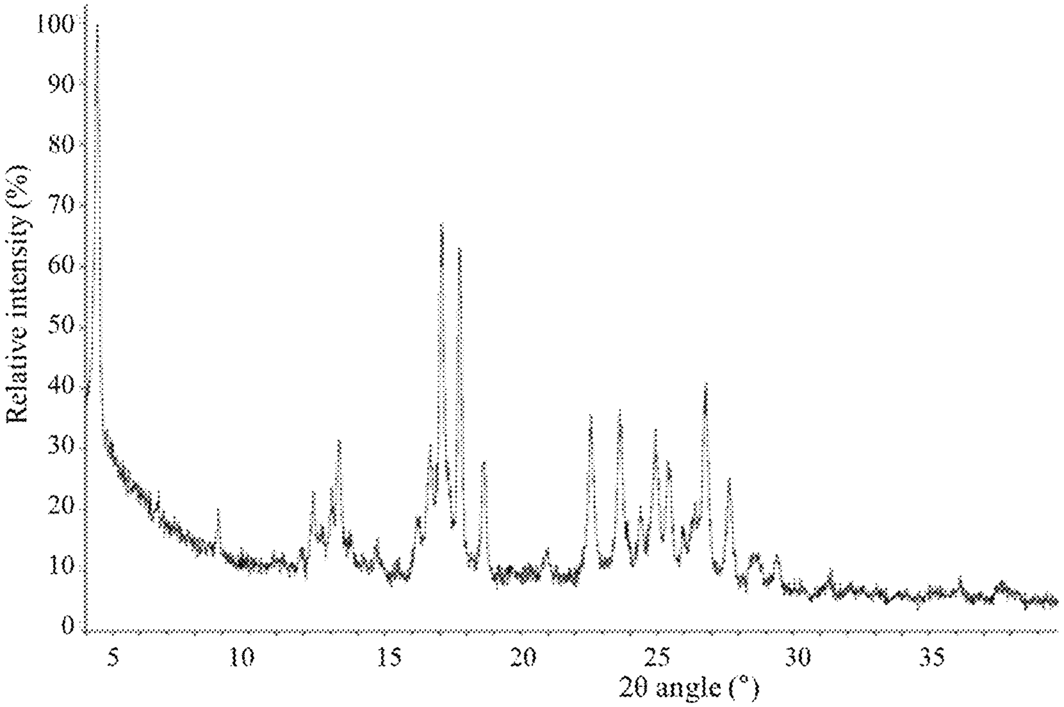
FIG. 10 is an XRPD pattern of the crystal form D of the compound of formula (IV) measured by Cu-Kα radiation.
Figure 11:
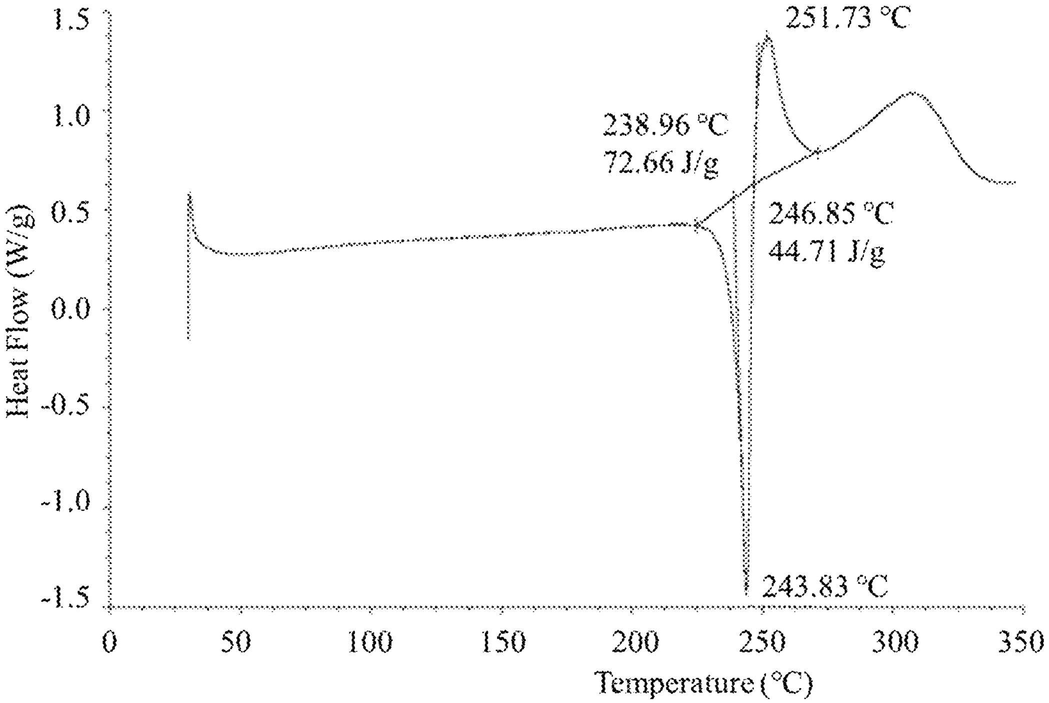
FIG. 11 is a DSC pattern of the crystal form D of the compound of formula (IV)
Figure 12:
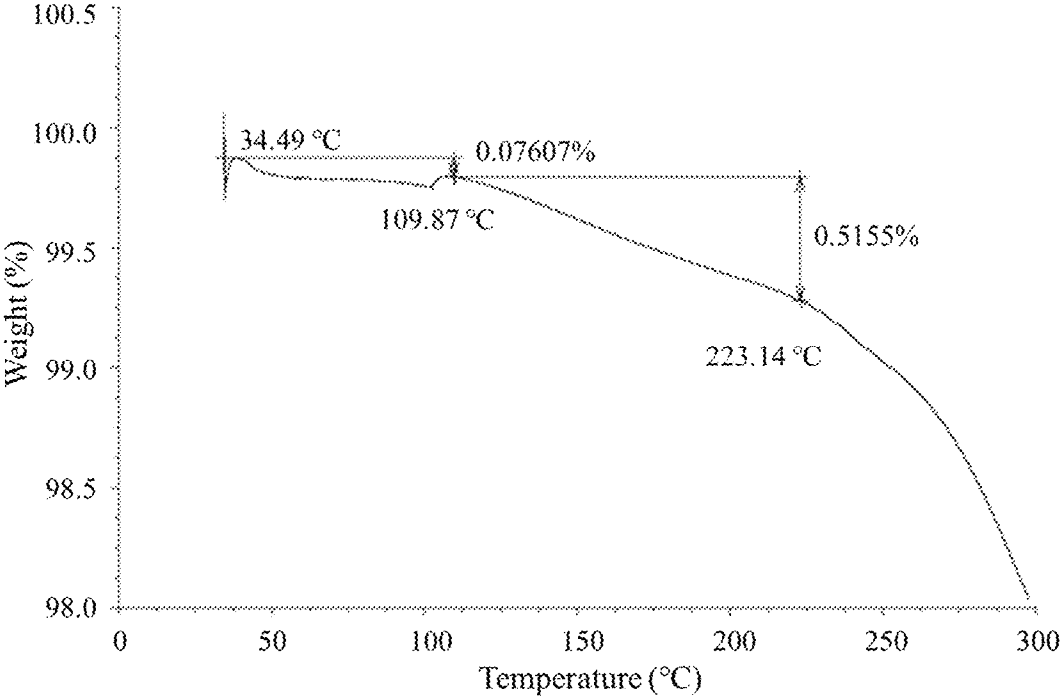
FIG. 12 is a TGA pattern of the crystal form D of the compound of formula (IV).
Figure 13:
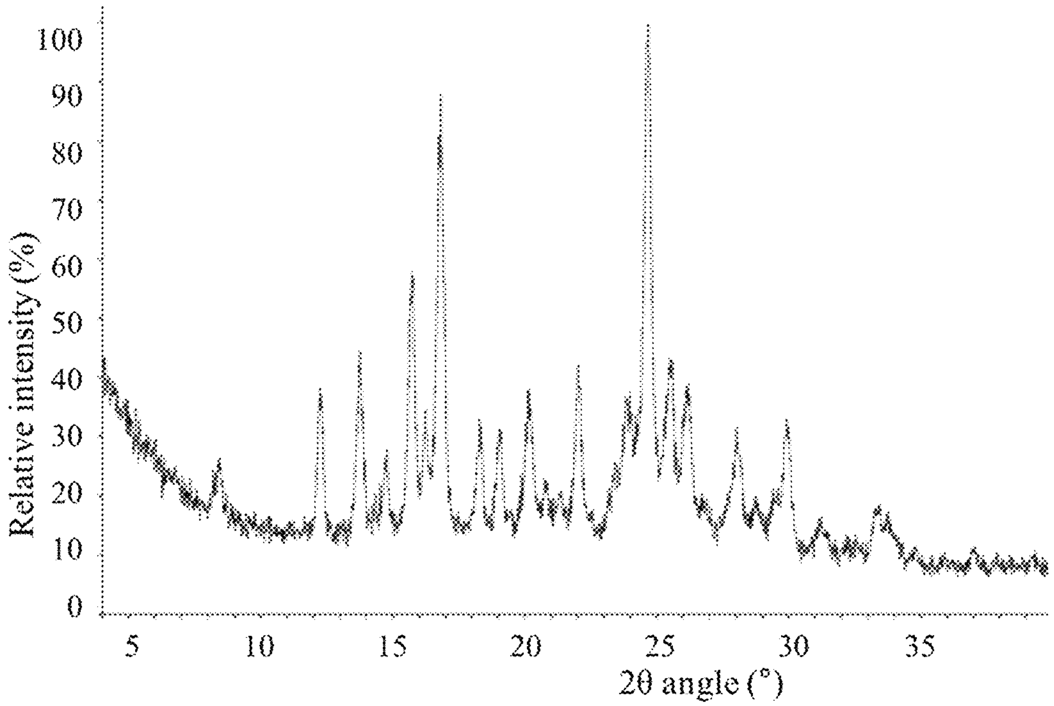
FIG. 13 is an XRPD pattern of the crystal form E of the compound of formula (V) measured by Cu-Kα radiation.
Figure 14:
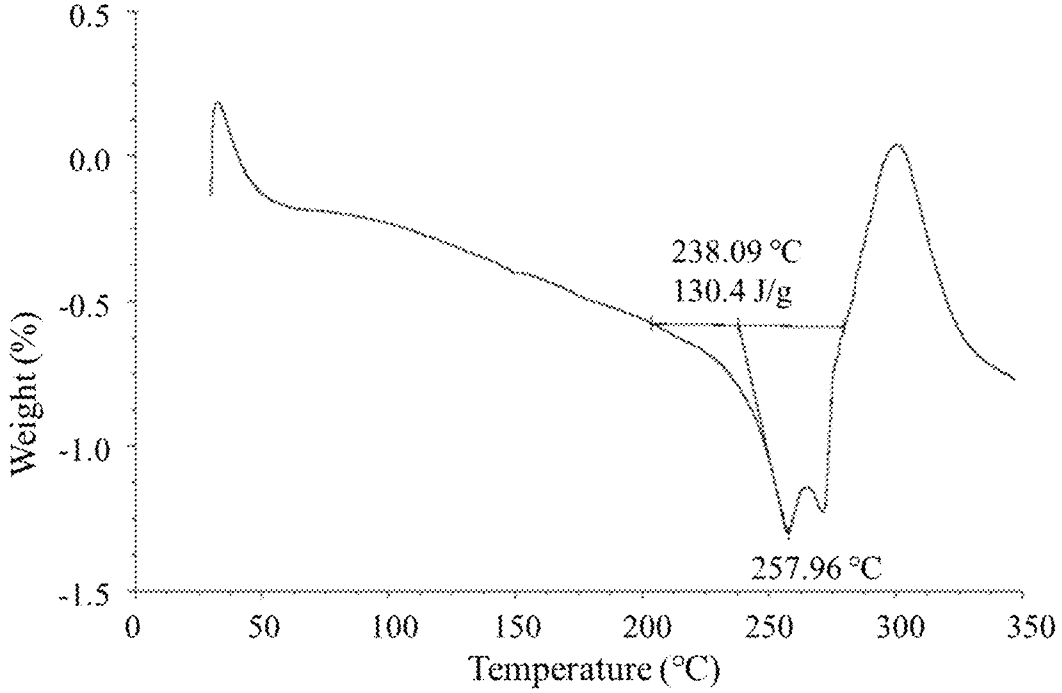
FIG. 14 is a DSC pattern of the crystal form E of the compound of formula (V)
Figure 15:
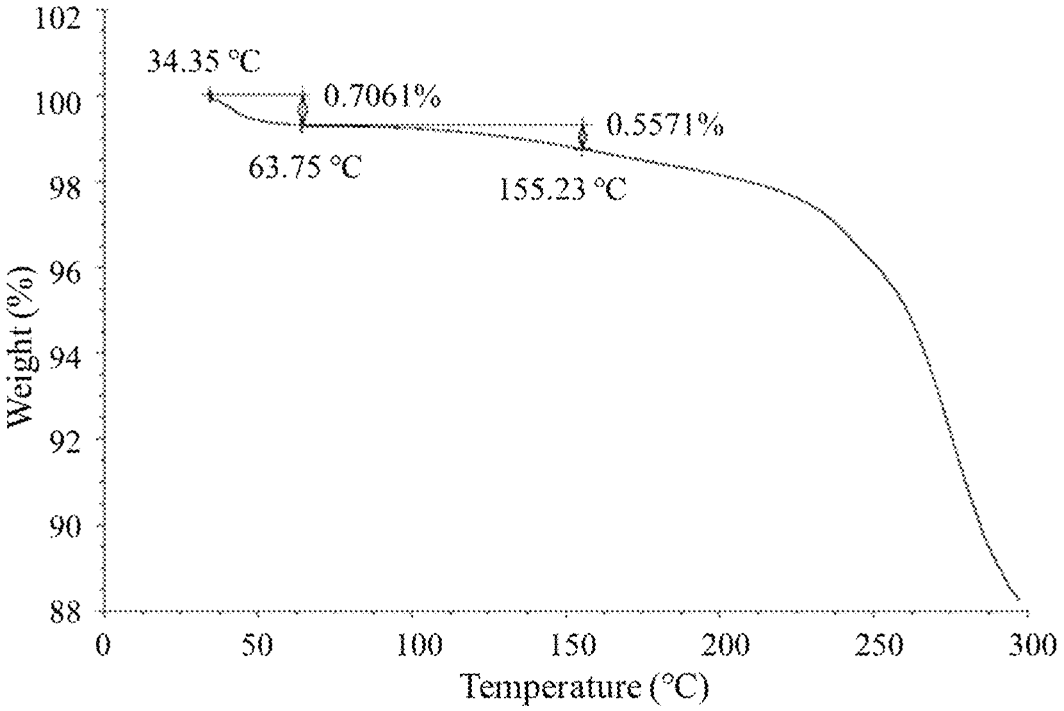
FIG. 15 is a TGA pattern of the crystal form E of the compound of formula (V).

4. The crystal form of the compound of formula (I) according to claim 3, wherein the XRPD pattern thereof is shown in FIG. 1;

or, a DSC pattern thereof is shown in FIG. 2;

or, a TGA pattern thereof is shown in FIG. 3.

* * * * *